US006639119B2

United States Patent
Roe et al.

(10) Patent No.: US 6,639,119 B2
(45) Date of Patent: Oct. 28, 2003

(54) ABSORBENT ARTICLE INCLUDING A REDUCING AGENT FOR FECES

(75) Inventors: Donald C. Roe, West Chester, OH (US); Brian R. White, Toronto (CA); John Christison, Mississauga (CA); Christopher P. Bewick-Sonntag, Pescara (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/899,716

(22) Filed: Jul. 5, 2001

(65) Prior Publication Data

US 2001/0053902 A1 Dec. 20, 2001

Related U.S. Application Data

(63) Continuation of application No. 09/106,395, filed on Jun. 29, 1998.

(51) Int. Cl.[7] ................................................ A61F 13/15
(52) U.S. Cl. ...................................... 604/367; 604/364
(58) Field of Search ................................. 604/364, 367, 604/368, 378, 359, 360; 252/174.12; 600/306, 345–350

(56) References Cited

U.S. PATENT DOCUMENTS

| | | |
|---|---|---|
| 2,773,000 A | 12/1956 | Masci et al. |
| 3,121,427 A | 2/1964 | Mosier |
| 3,490,454 A | 1/1970 | Goldfarb et al. |
| 3,661,154 A | 5/1972 | Torr |
| 3,670,731 A | 6/1972 | Harmon |
| 3,783,872 A | 1/1974 | King |
| 3,810,468 A | 5/1974 | Harper et al. |

(List continued on next page.)

FOREIGN PATENT DOCUMENTS

| | | |
|---|---|---|
| DE | 30 38 192 A1 | 12/1982 |
| EP | 0 249 391 | 12/1987 |
| EP | 0 268 459 | 5/1988 |
| EP | 0 386 897 | 9/1990 |
| EP | 0 420 248 A1 | 4/1991 |
| EP | 0 427 219 A2 | 5/1991 |
| EP | 0 640 328 A1 | 3/1995 |
| EP | 0 689 817 | 1/1996 |
| EP | 0 761 241 A2 | 3/1997 |
| EP | 0 792 653 A2 | 9/1997 |
| EP | 0 793 971 A1 | 9/1997 |
| GB | 1 550 614 | 8/1979 |
| GB | 1 576 475 | 10/1980 |
| JP | 54-004498 | 1/1979 |
| JP | 54-004500 | 1/1979 |
| JP | 04-178462 | 6/1992 |
| JP | 5237377 | 9/1993 |
| WO | WO 86/02543 | 5/1986 |
| WO | WO 94/13704 | 6/1994 |
| WO | WO 94/29325 | 12/1994 |
| WO | WO 97/38735 | 10/1997 |
| WO | WO 98/09662 | 3/1998 |
| WO | WO 98/37841 | 9/1998 |

*Primary Examiner*—Weilun Lo
*Assistant Examiner*—Jacqueline Stephens
(74) *Attorney, Agent, or Firm*—Ian S. Robinson; Ken K. Patel; Steven W. Miller

(57) ABSTRACT

An absorbent article adapted to receive feces having a first waist region, a second waist region opposed to the first waist region, a crotch region disposed between the first waist region and the second waist region, the absorbent article comprising: a liquid pervious topsheet; a liquid impervious backsheet joined to at least a portion of the topsheet; an absorbent core disposed between at least a portion of the topsheet and the backsheet, and an effective amount of a feces reducing agent disposed in the article such that the reducing agent is available to contact at least a portion of the feces deposited in the article.

14 Claims, 7 Drawing Sheets

U.S. PATENT DOCUMENTS

| | | | |
|---|---|---|---|
| 3,844,287 A | 10/1974 | Smith | |
| 3,875,942 A | 4/1975 | Roberts et al. | |
| 3,901,236 A | 8/1975 | Assarsson et al. | |
| 3,920,015 A | 11/1975 | Wortham | |
| 3,935,363 A | 1/1976 | Burkholder et al. | |
| 4,055,180 A | 10/1977 | Karami | |
| 4,077,410 A * | 3/1978 | Butterworth et al. | 128/287 |
| 4,084,591 A | 4/1978 | Takebe et al. | |
| 4,103,062 A | 7/1978 | Aberson et al. | |
| 4,117,184 A | 9/1978 | Erickson et al. | |
| 4,144,886 A | 3/1979 | Holst et al. | |
| 4,212,302 A | 7/1980 | Karami | |
| 4,296,234 A | 10/1981 | Mindt et al. | |
| 4,315,761 A | 2/1982 | Larrson et al. | |
| 4,318,408 A | 3/1982 | Korpman | |
| 4,342,858 A | 8/1982 | Herman et al. | |
| 4,366,294 A | 12/1982 | Williams et al. | |
| 4,381,784 A | 5/1983 | Aberson et al. | |
| 4,435,178 A | 3/1984 | Fitzgerald | |
| 4,556,560 A | 12/1985 | Buckingham | |
| 4,616,644 A | 10/1986 | Saferstein et al. | |
| 4,626,252 A | 12/1986 | Nishizawa et al. | |
| 4,631,132 A | 12/1986 | Jones | |
| 4,728,642 A | 3/1988 | Pawelchak et al. | |
| 4,753,643 A | 6/1988 | Kassai | |
| 4,790,836 A | 12/1988 | Brecher | |
| 4,842,593 A * | 6/1989 | Jordan et al. | 604/360 |
| 4,882,204 A | 11/1989 | Tenenbaum | |
| 5,080,657 A | 1/1992 | Lee et al. | |
| RE33,839 E | 3/1992 | Chmelir et al. | |
| 5,165,946 A | 11/1992 | Taylor et al. | |
| 5,197,945 A | 3/1993 | Cole et al. | |
| 5,246,596 A | 9/1993 | Baldwin, Jr. et al. | |
| 5,256,477 A | 10/1993 | Mahoney | |
| 5,260,345 A | 11/1993 | DesMarais et al. | |
| 5,360,419 A | 11/1994 | Chen et al. | |
| 5,364,636 A | 11/1994 | Ochi | |
| 5,409,771 A | 4/1995 | Dahmen et al. | |
| 5,468,236 A * | 11/1995 | Everhart et al. | 604/361 |
| 5,558,745 A | 9/1996 | Conway et al. | |
| 5,576,364 A | 11/1996 | Isaac et al. | |
| 5,599,916 A | 2/1997 | Dutkiewicz et al. | |
| 5,612,411 A | 3/1997 | Gross | |
| 5,624,564 A | 4/1997 | Blum | |
| 5,643,588 A * | 7/1997 | Roe et al. | 424/402 |
| 5,649,914 A * | 7/1997 | Glaug et al. | 604/361 |
| 5,663,286 A | 9/1997 | Ahmed et al. | |
| 5,685,872 A | 11/1997 | Syverson | |
| 5,716,337 A | 2/1998 | McCabe et al. | |
| 5,735,812 A | 4/1998 | Hardy | |
| 5,753,252 A * | 5/1998 | Brown-Skrobot | 424/431 |
| 5,801,220 A | 9/1998 | Desai et al. | |
| 5,868,723 A * | 2/1999 | Al-Sabah | 604/361 |
| 5,968,025 A * | 10/1999 | Roe et al. | 604/364 |
| 5,998,695 A * | 12/1999 | Roe et al. | 604/367 |
| 6,046,243 A * | 4/2000 | Wellinghoff et al. | 514/772.3 |
| 6,060,636 A * | 5/2000 | Yahiaoui et al. | 604/367 |

* cited by examiner

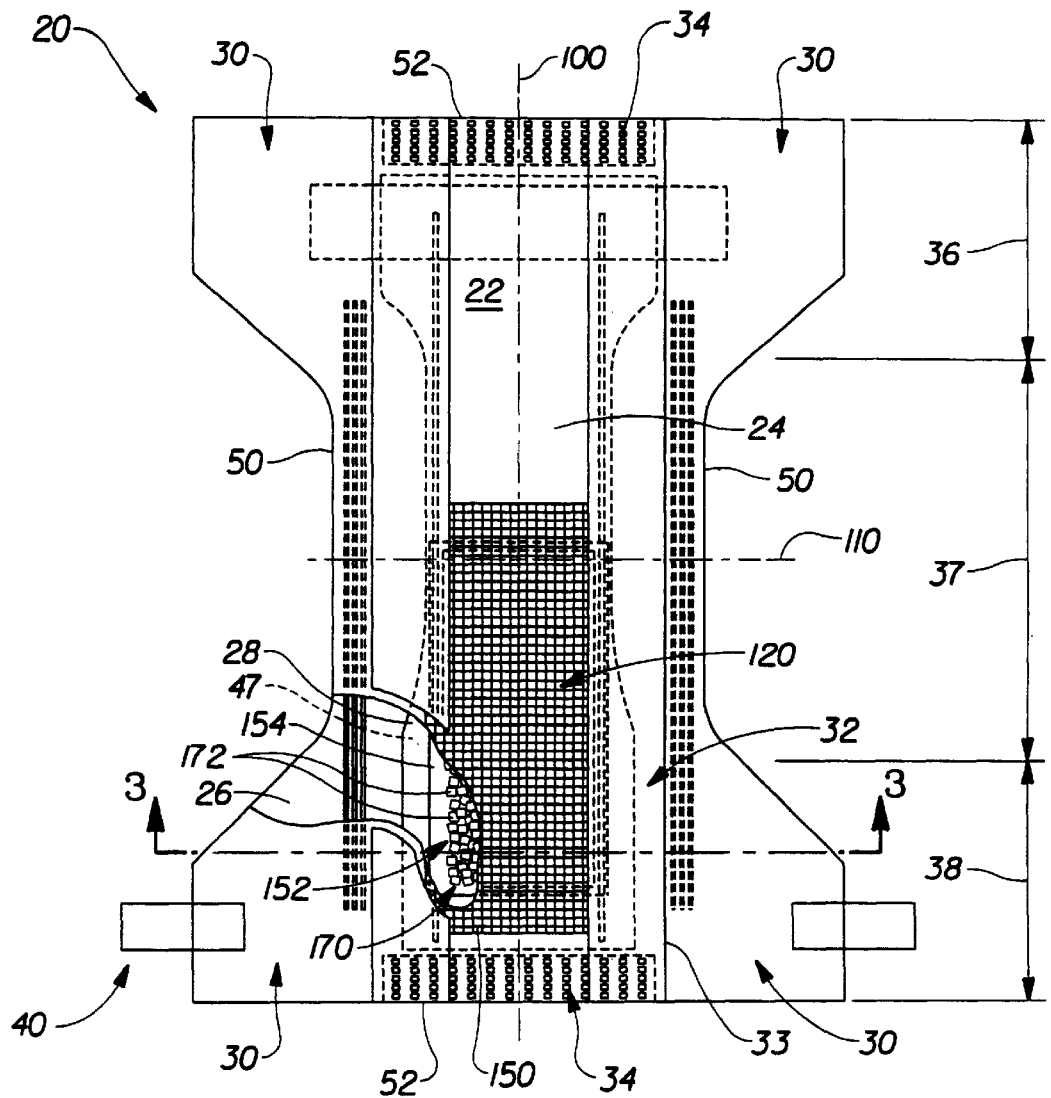
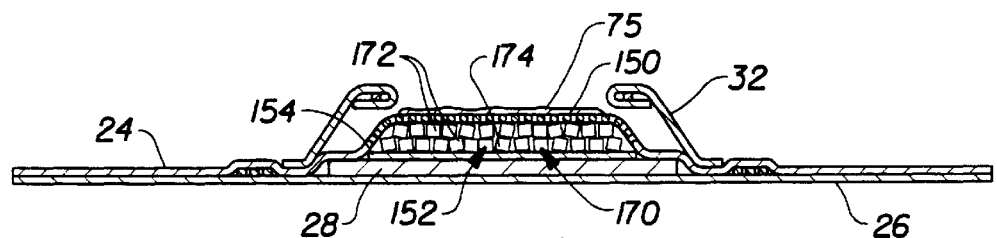
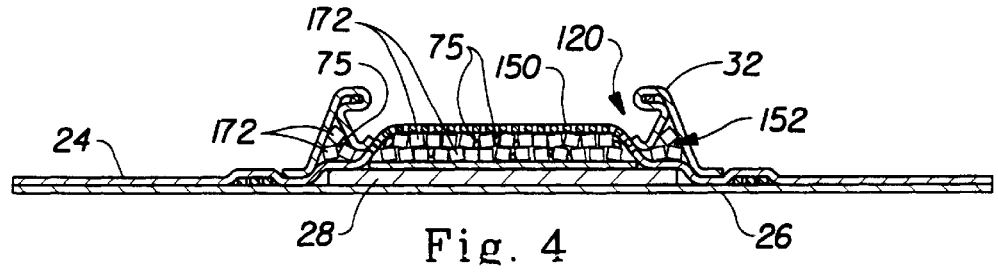
Fig. 2
Fig. 3
Fig. 4

ABSORBENT ARTICLE INCLUDING A REDUCING AGENT FOR FECES

CROSS REFERENCE

This is a continuation under 35 U.S.C. §120 of patent applications Ser. No. 09/106,395, filed Jun. 29, 1998.

FIELD OF THE INVENTION

The present invention relates to articles which absorb and/or contain bodily exudates, including disposable absorbent articles such as diapers, adult incontinence products, sanitary napkins and the like. More particularly, the invention relates to disposable absorbent articles including one or more reducing agents which act to modify the physical properties of feces or other bodily wastes which may be deposited in the article.

BACKGROUND OF THE INVENTION

The major function of absorbent articles such as diapers and adult incontinence briefs is to prevent body exudates from soiling, wetting, or otherwise contaminating clothing or other articles, such as bedding, that may come in contact with the wearer. In recent years, disposable diapers, such as those disclosed in U.S. Pat. No. 5,151,092 issued to Buell et al., have become very popular and have generally replaced durable cloth absorbent articles because of their convenience and reliability. However, despite the effectiveness of such disposable absorbent articles, body exudates often still leak or are stored in the diaper such that the exudates soil and/or irritate the skin of the wearer. Additionally, body exudates often adhere aggressively to skin, increasing the difficulty of cleaning and increasing the likelihood of chronic residual contamination. The fundamental causes of these, and other key problems with absorbent articles of the art lie in the high viscosity of feces and the tenacity with which they hold their constituent water. These factors greatly inhibit the absorption of feces by conventional absorbent articles.

The undesirable effects of leakage and/or improper containment, difficult cleanup, and/or residual skin contamination are especially evident with regard to fecal matter deposited in the diaper. Feces contained in the diaper can harm the skin of the wearer over time and feces leaking from the diaper almost invariably presents unpleasant, messy clean-ups. Thus, several attempts have been made to add features to diapers such as barriers, pockets, spacers, transverse barriers, apertured topsheets and the like to limit the movement of the fecal material across the topsheet and/or to better confine the fecal matter in the diaper. However, such attempts have been generally unsuccessful because they fail to address the fundamental causes of these problems (i.e., the properties of feces) and, because of their cost and complexity. Further, many of the means for isolating or containing feces are directed to fecal material with certain physical properties (e.g., viscosity, free water content and particle size) and are not effective with exudates with physical properties outside a very small range.

Chemical agents have been employed in superabsorbent polymer particles to attempt to increase the osmotic potential of the polymer for purposes of increasing the effective capacity of the superabsorbent for urine. For example, EP 0420248 A1 describes the use of osmotic materials encased in chambers inside superabsorbent polymer particles to increase absorptive capacity. In such cases, however, the osmotic material is not available to contact any surrounding fecal material and thus, does not function as a feces modification agent as described herein.

U.S. Pat. No. 4,556,560 teaches the use of certain metal salts as lipase inhibitors. These agents are affixed to the topsheet via deposition using a volatile solvent. As taught, a urine voiding is required to wet the topsheet and release the lipase inhibiting agent. Also, the lipase inhibitors may be washed into the absorbent core as part of the urine gush. These factors clearly limit the accessibility of the agent by the fecal material.

U.S. Pat. No. 4,790,836 discloses a diaper including layer of medicated powder located between the absorbent core and a water-soluble film. The medicated powder is used to promote drying of the infant's skin after the wearer wets the diaper. However, as shown in Table II, below, the embodiments disclosed in this patent do not function to provide the feces modification benefit of the present invention.

Accordingly, it would be desirable to provide an absorbent article with improved feces management properties. Further, it would be advantageous to provide an economical disposable article with the ability to minimize the negative effects of feces or other viscous bodily waste on the wearer or the caregiver. It would also be advantageous to provide an article which is designed to chemically or physically interact with the feces and to change the properties of the feces in order to improve acceptance of feces into the article and/or immobilization of the feces within the article and/or reduce the contamination of the wearer's skin with feces. Also, it would be desirable to provide an article having sufficient effective capacity and retention capability to store the physically or chemically modified feces safely and cleanly away from the wearer's skin and/or clothing throughout the expected time of use.

SUMMARY OF THE INVENTION

In order to help resolve at least some of the problems described above and otherwise found in the absorbent articles of the prior art, the present invention provides an article including a reducing agent which is available in an effective concentration to physically or chemically modify some or all of the fecal material or other bodily exudates deposited in the article. The modification of the feces may improve acceptance and/or retention of the exudates within the article to reduce the spreading of fecal material within the diaper and/or to reduce the tendency of the fecal material to adhere to the wearer's skin. The present invention also provides an absorbent article capable of accepting, storing and/or immobilizing the exudates in their modified form to reduce the likelihood that the waste will migrate back toward the wearer's skin once the waste is imbibed by the article. Accordingly, the absorbent article of the present invention may reduce the likelihood of harm to the wearer's skin and/or the inconvenience to the caregiver normally associated with bowel movements.

BRIEF DESCRIPTION OF THE DRAWINGS

While the specification concludes with claims particularly pointing out and distinctly claiming the subject matter which is regarded as the present invention, it is believed that the description will be better understood from the following descriptions which are taken in conjunction with the accompanying drawings in which like designations are used to designate substantially identical elements.

FIG. 2 is a plan view of an absorbent article embodiment of the present invention having portions cut away to reveal the underlying structure, the body-facing surface of the diaper facing the viewer.

FIG. 3 is a cross sectional view of an absorbent article embodiment of the present invention taken through the section lines 3—3.

FIG. 4 is a cross sectional view of an alternative embodiment of an absorbent article of the present invention.

DETAILED DESCRIPTION OF THE INVENTION

As used herein, the term "absorbent article" refers to devices which absorb and contain body exudates, and more specifically, refers to devices which are placed against or in proximity to the body of the wearer to absorb and contain the various exudates discharged from the body. The term "disposable" is used herein to describe absorbent articles which generally are not intended to be laundered or otherwise restored or reused as an absorbent article (i.e., they are intended to be discarded after a single use and, preferably, to be recycled, composted or otherwise disposed of in an environmentally compatible manner). (As used herein, the term "disposed" is used to mean that an element(s) of the diaper is formed (joined or positioned) in a particular place or position as a unitary structure with other elements of the diaper or as a separate element joined to another element of the diaper. As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.) A "unitary" absorbent article refers to absorbent articles which are formed of separate parts united together to form a coordinated entity so that they do not require separate manipulative parts like a separate holder and liner.

Figure 1:
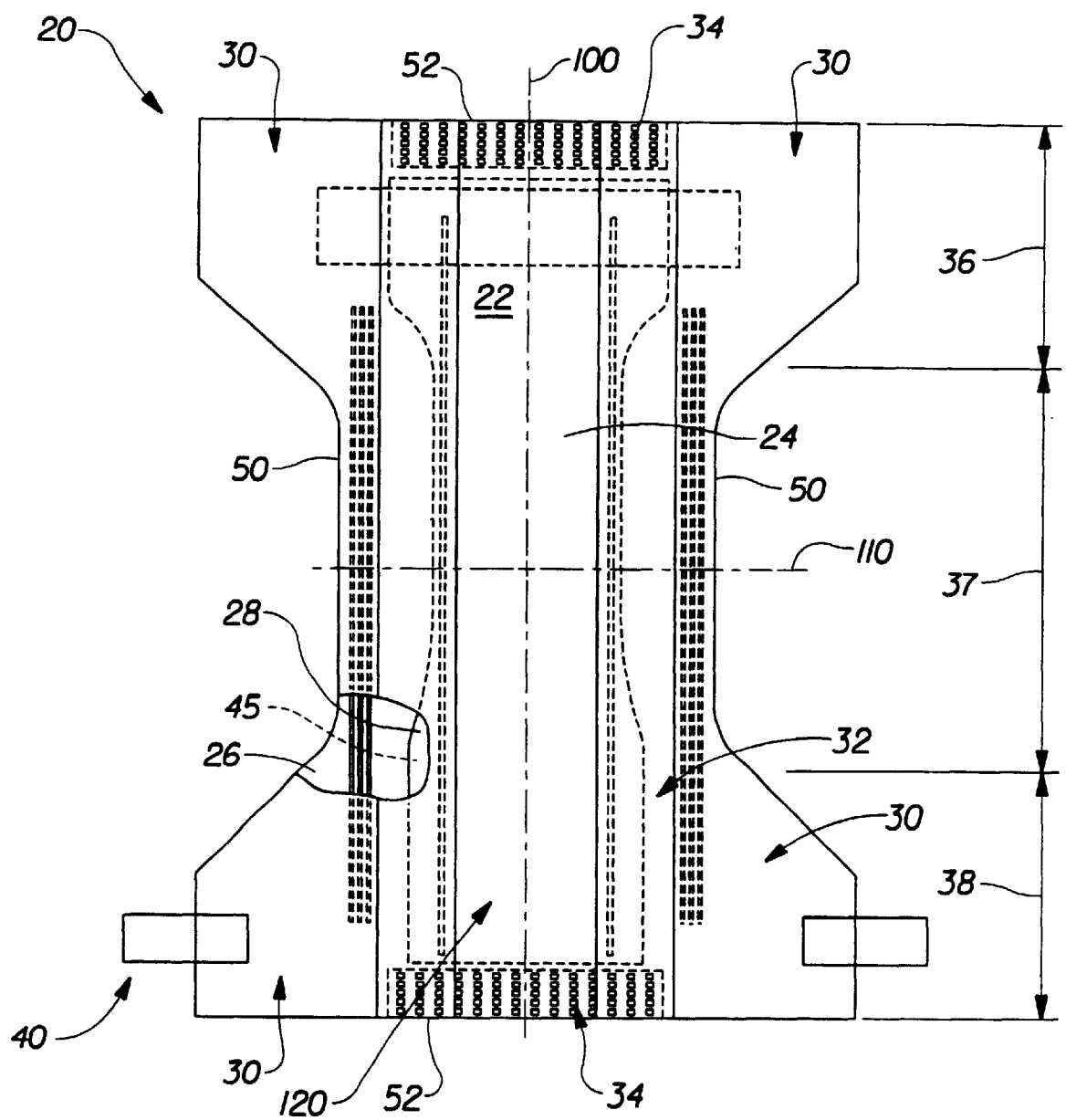
FIG. 1 is a plan view of an absorbent article embodiment of the present invention having portions cut away to reveal the underlying structure, the body-facing surface of the diaper facing the viewer.

A preferred embodiment of an absorbent article of the present invention is the unitary disposable absorbent article, diaper 20, shown in FIG. 1. (As used herein, the term "diaper" refers to an absorbent article generally worn by infants and incontinent persons about the lower torso.) However, the present invention is also applicable to other absorbent articles such as incontinence briefs, incontinence undergarments, absorbent inserts, diaper holders and liners, feminine hygiene garments, wipes, mops, bandages and the like. The present invention is also applicable to absorbent or nonabsorbent feces collection devices which can be separately applied to the wearer's perianal region.

FIG. 1 is a plan view of the diaper 20 of the present invention in a flat-out, state with portions of the structure being cut-away to more clearly show the construction of the diaper 20. The portion of the diaper 20 which faces the wearer is oriented towards the viewer. As shown in FIG. 1, the diaper 20 preferably comprises a liquid pervious topsheet 24; a liquid impervious backsheet 26; an absorbent core 28, which is preferably positioned between at least a portion of the topsheet 24 and the backsheet 26; side panels 30; elasticized leg cuffs 32; an elastic waist feature 34; and a fastening system generally designated 40. Diaper 20 is shown in FIG. 1 to have a first waist region 36, a second waist region 38 opposed to the first waist region 36 and a crotch region 37 located between the first waist region and the second waist region. The periphery of the diaper 20 is defined by the outer edges of the diaper 20 in which the longitudinal edges 50 run generally parallel to the longitudinal centerline 100 of the diaper 20 and the end edges 52 run between the longitudinal edges 50 generally parallel to the lateral centerline 110 of the diaper 20.

The chassis 22 of the diaper 20 comprises the main body of the diaper 20. The chassis 22 comprises at least a portion of the absorbent core 28 and preferably an outer covering layer including the topsheet 24 and the backsheet 26. If the absorbent article comprises a separate holder and a liner, the chassis 22 generally comprises the holder and the liner. (For example, the holder may comprise one or more layers of material to form the outer cover of the article and the liner may comprise an absorbent assembly including a topsheet, a backsheet, and an absorbent core. In such cases, the holder and/or the liner may include a fastening element which is used to hold the liner in place throughout the time of use.) For unitary absorbent articles, the chassis 22 comprises the main structure of the diaper with other features added to form the composite diaper structure.

While the topsheet 24, the backsheet 26, and the absorbent core 26 may be assembled in a variety of well known configurations, preferred diaper configurations are described generally in U.S. Pat. No. 3,860,003 entitled "Contractible Side Portions for Disposable Diaper" which issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554, 145 entitled "Absorbent Article With Multiple Zone Structural Elastic-Like Film Web Extensible Waist Feature" which issued to Roe et al. on Sep. 10, 1996; U.S. Pat. No. 5,569,234 entitled "Disposable Pull-On Pant" which issued to Buell et al. on Oct. 29, 1996; and U.S. Pat. No. 5,580,411 entitled "Zero Scrap Method For Manufacturing Side Panels For Absorbent Articles" which issued to Nease et al. on December 3; each of which is incorporated herein by reference.

The backsheet 26 is generally that portion of the diaper 20 positioned adjacent the garment facing surface 45 of the absorbent core 28 which prevents the exudates absorbed and contained therein from soiling articles which may contact the diaper 20, such as bedsheets and undergarments. In preferred embodiments, the backsheet 26 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962 and X10964. Other suitable backsheet materials may include breathable materials which permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by Exxon Chemical Co., of Bay City, Tex., under the designation EXXAIRE. Suitable breathable composite materials comprising polymer blends are available from Clopay Corporation, Cincinnati, Ohio under the name HYTREL blend P18-3097. Some breathable composite materials are described in greater detail in PCT Application No. WO 95/16746, published on Jun. 22, 1995 in the name of E.I. DuPont and copending U.S. patent application Ser. No. 08/744,487, now U.S. Pat. No. 5,865,823 filed on Nov. 6, 1996 in the name of Curro. Other breathable backsheets including nonwoven webs and apertured formed films are described in U.S. Pat. No. 5,571,096 issued to Dobrin et al. on Nov. 5, 1996. Each of these references is hereby incorporated by reference herein.

The backsheet 26, or any portion thereof, may be elastically extensible in one or more directions. In one embodiment, the backsheet 26 may comprise a structural elastic-like film ("SELF") web as described in U.S. Pat. No. 5,518,801 entitled Web Materials Exhibiting Elastic-Like Behavior, which issued to Chappell, et, al. on May 21, 1996, which is incorporated herein by reference. In alternate embodiments, the backsheet 26 may comprise elastomeric films, foams, strands, or combinations of these or other suitable materials with nonwovens or synthetic films.

The backsheet 26 may be joined to the topsheet 24, the absorbent core 28 or any other element of the diaper 20 by any attachment means known in the art. For example, the attachment means may include a uniform continuous layer of adhesive, a patterned layer of adhesive, or an array of separate lines, spirals, or spots of adhesive. Alternatively, the attachment means may comprise heat bonds, pressure bonds, ultrasonic bonds, dynamic mechanical bonds, or any other suitable attachment means or combinations of these attachment means as are known in the art.

The topsheet 24 is preferably compliant, soft feeling, and non-irritating to the wearer's skin. Further, at least a portion of the topsheet 24 is liquid pervious, permitting liquids to readily penetrate through its thickness. A suitable topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. If the topsheet includes fibers, the fibers may be spunbond, carded, wet-laid, meltblown, hydroentangled, or otherwise processed as is known in the art. One suitable topsheet 24 comprising a web of staple length polypropylene fibers is manufactured by Veratec, Inc., a Division of International Paper Company, of Walpole, Mass. under the designation P-8.

Suitable formed film topsheets are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr, et al. on Jul. 31, 1984; and U.S. Pat. No. 5,006,394 "Multilayer Polymeric Film" issued to Baird on Apr. 9, 1991. Other suitable topsheets 30 are made in accordance with U.S. Pat. Nos. 4,609,518 and 4,629,643 which issued to Curro et al. on Sep. 2, 1986 and Dec. 16, 1986, respectively, and both of which are incorporated herein by reference. Such formed films are available from The Procter & Gamble Company of Cincinnati, Ohio as "DRI-WEAVE" and from Tredegar Corporation of Terre Haute, Ind. as "CLIFF-T."

The topsheet 24 may be made of a hydrophobic material or be treated to be hydrophobic in order to isolate the wearer's skin from liquids contained in the absorbent core 28. If the topsheet 24 is made of a hydrophobic material, preferably at least the upper surface of the topsheet 24 is treated to be hydrophilic so that liquids will transfer through the topsheet more rapidly. This diminishes the likelihood that body exudates will flow off the topsheet 24 rather than being drawn through the topsheet 24 and being absorbed by the absorbent core 28. The topsheet 24 can be rendered hydrophilic by treating it with a surfactant or by incorporating a surfactant into the topsheet. Suitable methods for treating the topsheet 24 with a surfactant or incorporating a surfactant in a topsheet are described in U.S. Pat. No. 4,988,344 entitled "Absorbent Articles with Multiple Layer Absorbent Layers" issued to Reising, et al. on Jan. 29, 1991 and U.S. Pat. No. 4,988,345 entitled "Absorbent Articles with Rapid Acquiring Absorbent Cores" issued to Reising on Jan. 29, 1991, and U.S. Statutory Invention Registration No. H1670, published on Jul. 1, 1997 in the names of Aziz et al. Each of these references is hereby incorporated by reference herein. Alternatively, the topsheet 24 may include an apertured web or film which is hydrophobic. This may be accomplished eliminating the hydrophilizing treatment step from the production process and/or applying a hydrophobic treatment to the topsheet 24, such as a polytetraflouroethylene compound like SCOTCHGUARD or a hydrophobic lotion composition, as described below. In such embodiments, it is preferred that the apertures be large enough to allow the penetration of aqueous fluids like urine without significant resistance.

Any portion of the topsheet 24 may be coated with a lotion as is known in the art. Examples of suitable lotions include those described in U.S. Pat. Nos. 5,607,760 entitled "Disposable Absorbent Article Having A Lotioned Topsheet Containing an Emollient and a Polyol Polyester Immobilizing Agent" which issued to Roe on Mar. 4, 1997; U.S. Pat. No. 5,609,587 entitled "Diaper Having A Lotion Topsheet Comprising A Liquid Polyol Polyester Emollient And An Immobilizing Agent" which issued to Roe on Mar. 11, 1997; U.S. Pat. No. 5,635,191 entitled "Diaper Having A Lotioned Topsheet Containing A Polysiloxane Emollient" which issued to Roe et al. on Jun. 3, 1997; and U.S. Pat. No. 5,643,588 entitled "Diaper Having A Lotioned Topsheet" which issued to Roe et al. on Jul. 1, 1997. The lotion may function alone or in combination with another agent as the hydrophobizing treatment described above. The topsheet may also include or be treated with antibacterial agents, some examples of which are disclosed in PCT Publication No. WO 95/24173 entitled "Absorbent Articles Containing Antibacterial Agents in the Topsheet For Odor Control" which was published on Sep. 14, 1995 in the name of Theresa Johnson. Further, the topsheet 24, the backsheet 26 or any portion of the topsheet or backsheet may be embossed and/or matte finished to provide a more cloth like appearance.

The topsheet 24 is preferably positioned adjacent the body surface 47 of the absorbent core 28 and may be joined thereto and/or to the backsheet 26 by any attachment means known in the art. Suitable attachment means are described above with respect to means for joining the backsheet 26 to other elements of the diaper 20.

The absorbent core 28 may comprise any absorbent material known in the art. The absorbent core 28 may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The configuration and construction of the absorbent core 28 may also be varied (e.g., the absorbent core(s) or other absorbent structure(s) may have varying caliper zones, a hydrophilic gradient, a superabsorbent gradient, or lower average density and lower average basis weight acquisition zones; or may comprise one or more layers or structures). However, the total absorbent capacity of the absorbent core 28 should be compatible with the design loading and the intended use of the diaper 20.

Exemplary absorbent structures for use as the absorbent core are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735, entitled "High Density Absorbent Members Having Lower Density and Lower Basis Weight Acquisition Zones", issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" which issued to Herron et al. on Aug. 11, 1992; U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994; U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; and U.S. Pat. No. 5,625,222 entitled "Absorbent Foam Materials For Aqueous Fluids Made From high Internal Phase Emulsions Having Very High Water-To-Oil Ratios" issued to DesMarais et al. on Jul. 22, 1997. Each of these patents is incorporated herein by reference.

The diaper 20 may also comprise one or more waist features 34 to help provide improved fit and containment. The elastic waist feature 34 may be constructed in a number of different configurations including those described in U.S. Pat. No. 4,515,595 issued to Kievit et al. on May 7, 1985; U.S. Pat. No. 4,710,189 issued to Lash on Dec. 1, 1987; U.S. Pat. No. 5,151,092 issued to Buell on Sep. 9, 1992; and U.S. Pat. No. 5,221,274 issued to Buell on Jun. 22, 1993. Other suitable waist configurations may include waistcap features such as those described in U.S. Pat. No. 5,026,364 issued to Robertson on Jun. 25, 1991 and U.S. Pat. No. 4,816,025 issued to Foreman on Mar. 28, 1989. All of the above mentioned references are incorporated herein by reference.

The diaper 20 may also include a fastening system 40. The fastening system 40 preferably maintains the first waist region 36 and the second waist region 38 in an overlapping configuration so as to provide lateral tensions about the circumference of the diaper 20 to hold the diaper 20 on the wearer. The fastening system 40 preferably comprises tape tabs and/or hook and loop fastening components, although any other known fastening means are generally acceptable. Some exemplary fastening systems are disclosed in U.S. Pat. No. 3,848,594 entitled "Tape Fastening System for Disposable Diaper" issued to Buell on Nov. 19, 1974; U.S. Pat. No. B1 4,662,875 entitled "Absorbent Article" issued to Hirotsu et al. on May 5, 1987; U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; and the herein before referenced U.S. Pat. No. 5,151, 092 issued to Buell on Sep. 9, 1992; and U.S. Pat. No. 5,221,274 issued to Buell on Jun. 22, 1993. The fastening system may also provide a means for holding the article in a disposal configuration as disclosed in U.S. Pat. No. 4,963, 140 issued to Robertson et al. on Oct. 16, 1990. Each of these patents is incorporated herein by reference. Some exemplary hooks are available from Aplix under the trade names 960E and 960D. Exemplary suitable loops are available from 3M under the trade name EBL and from Guilford under the trade designation 18904. In alternative embodiments, opposing sides of the garment may be seamed or welded to form a pant so as to allow the article to be used as a pull-on type diaper, such as a training pant.

The diaper 20 may also include side panels 30 constructed and joined to the chassis in any suitable configuration. Examples of diapers with elasticized side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; the herein before referenced U.S. Pat. No. 5,151,092 issued to Buell on Sep. 9, 1992; and U.S. Pat. No. 5,221,274 issued to Buell on Jun. 22, 1993; U.S. Pat. No. 5,669,897 issued to LaVon, et al. on Sep. 23, 1997 entitled "Absorbent Articles Providing Sustained Dynamic Fit"; EPO Publication No. WO 95/13775 A1, published May 26, 1995 entitled "Absorbent Article With Multi-Directional Extensible Side Panels"; each of which is incorporated herein by reference.

The diaper 20 preferably further includes leg cuffs 32 to help provide improved containment of liquids and other body exudates. Leg cuffs may also be referred to as leg bands, side flaps, barrier cuffs, or elastic cuffs. U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. on Feb. 28, 1989 and Mar. 20, 1990, respectively, describe disposable diapers having "stand-up" elasticized flaps (barrier cuffs) which improve the containment of the leg regions. U.S. Pat. Nos. 4,695,278 and 4,795,454 issued to Lawson on Sep. 22, 1987 and to Dragoo on Jan. 3, 1989, respectively, describe disposable diapers having dual cuffs, including gasketing cuffs and barrier cuffs. In some embodiments, it may be desirable to treat all or a portion of the leg cuffs with a lotion, as described above.

Embodiments of the present invention may also include pockets for receiving and containing waste, spacers which provide voids for waste, barriers for limiting the movement of waste in the article, compartments or voids which accept and contain waste materials deposited in the diaper, and the like, or any combinations thereof. Examples of pockets and spacers for use in absorbent products are described in U.S. Pat. No. 5,514,121 issued to Roe et al. on May 7, 1996, entitled "Diaper Having Expulsive Spacer"; U.S. Pat. No. 5,171,236 issued to Dreier et al on Dec. 15, 1992, entitled "Disposable Absorbent Article Having Core Spacers"; U.S. Pat. No. 5,397,318 issued to Dreier on Mar. 14, 1995, entitled "Absorbent Article Having A Pocket Cuff"; U.S. Pat. No. 5,540,671 issued to Dreier on Jul. 30, 1996, entitled "Absorbent Article Having A Pocket Cuff With An Apex"; and PCT Application WO 93/25172 published Dec. 3, 1993, entitled "Spacers For Use In Hygienic Absorbent Articles And Disposable Absorbent Articles Having Such Spacer"; and U.S. Pat. No. 5,306,266, entitled "Flexible Spacers For Use In Disposable Absorbent Articles", issued to Freeland on Apr. 26, 1994. Examples of compartments or voids are disclosed in U.S. Pat. No. 4,968,312, entitled "Disposable Fecal Compartmenting Diaper", issued to Khan on Nov. 6, 1990; U.S. Pat. No. 4,990,147, entitled "Absorbent Article With Elastic Liner For Waste Material Isolation", issued to Freeland on Feb. 5, 1991; U.S. Pat. No. 5,62,840, entitled "Disposable Diapers", issued to Holt et al on Nov. 5, 1991; and U.S. Pat. No. 5,269,755 entitled "Trisection Topsheets For Disposable Absorbent Articles And Disposable Absorbent Articles Having Such Trisection Topsheets", issued to Freeland et al on Dec. 14, 1993. Examples of suitable transverse barriers are described in U.S. Pat. No. 5,554,142 entitled "Absorbent Article Having Multiple Effective Height Transverse Partition" issued Sep. 10, 1996 in the name of Dreier et al.; PCT Patent WO 94/14395 entitled "Absorbent Article Having An Upstanding Transverse Partition" published Jul. 7, 1994 in the name of Freeland, et al.; and U.S. Pat. No. 5,653,703 Absorbent Article Having Angular Upstanding Transverse Partition, issued Aug. 5, 1997 to Roe, et al. All of the above-cited references are hereby incorporated by reference herein.

The article of the present invention may also include one or more feces modifying agents ("FMAs", "viscous bodily waste modifying agents", "modifying agents" or "agents") in an effective concentration capable of modifying the chemical or physical properties of viscous bodily waste, such as feces and menses. As used herein, "feces modifying agent" (or FMA) refers to any chemical composition capable of increasing the hardness of a given fecal analog, or preferably actual feces, by at least about 100% or decreasing the hardness of a given fecal analog, or preferably actual feces, by at least about 25%, as measured by the Hardness Method, described below. Depending on the particular article design and the type of feces, embodiments are contemplated which increase or decrease the effective viscosity of feces, increase or decrease the ease of dewatering the feces, decrease the stickiness or adhesion characteristics of the feces, or any combination of the above. Although the feces modifying agents of the present invention may be capable of modifying the properties of solid feces, the FMAs are generally most effective in altering the properties of viscous fluid feces which generally have a viscosity of greater than about 10 cP and less than about $10^7$ cP at a shear rate of one 1/sec, (at about 35 degrees C.), and more particularly between about $10^2$ cP and $10^7$ cP at a one 1/sec shear rate, in a controlled stress rheometry test using parallel plates on a controlled stress rheometer. (For reference, water is at 1.0 cP at 20 degrees C. and Jif Creamy peanut butter (available from the Procter & Gamble Co., Cinti., Ohio) is approximately $4 \times 10^5$ cP at 25 degrees C. at this same shear rate). The method for determining viscosity, as used herein, is described in detail in the Test Methods section below.

Regardless of the specific effect of the chemical agent on feces, the agent must be available to the feces in order to perform its function. As used herein, in the context of FMAs, the term "available" indicates that the agent is positioned within the article or presented by the article or a component of the article during the course of normal wearing of the article so as to directly contact at least a portion of the feces deposited in the article or on the wearer's skin. If the agent is positioned within a structure (e.g., in an absorbent layer under a topsheet), the structure must be substantially penetrable by the feces. In such cases, the agent is "available" if the structure has an Acceptance Under Pressure greater than about 0.50 g/cm2/J, and preferably greater than about 1.0 g/cm2/J, as measured by the Acceptance measurement described in the Methods section below. If the agent is encapsulated, it should be released by the article at or about the time when the feces insults the article. For example, the FMA may be retained by a water-soluble film which, upon contact with urine or fecal water, dissolves and releases the FMA to contact the feces.

An "effective concentration" of an FMA, as used herein, refers to the relative amount of the agent required to have a measurable effect on the Hardness (as measured by the Hardness Method described below) of at least a portion of the feces in the article or on the skin of the wearer. Data illustrating an "effective concentration" is provided below. Preferably, a concentration of a FMA of at least about 0.01 weight percent of the feces to be treated is desirable, and more typically between about 0.1 and about 50 weight percent of the feces is available to the feces. For example, to treat an entire 25 gram feces loading in a diaper (i.e., a "bulk" treatment) at a 5 weight percent level, 1.25 grams of the FMA must be available to the fecal mass (assuming the specific gravity of the feces is 1.0). Thus, the FMA is preferably present in the article in concentrations ranging from about 0.001% to about 50% by weight of the article. Typically, however, the concentration is between about 0.01 and about 20 weight percent of the article.

The FMA is preferably capable of reducing the Hardness of a fecal analog, and preferably actual feces, by about 25% (and preferably about 50%) at a concentration of no more than about 20 weight percent of the feces to be treated at room temperature (20–25° C.). More preferably, the FMA is capable of reducing the Hardness of a fecal analog or actual feces by about 25% (and preferably about 50%) at a concentration of no more than about 10 weight percent of the feces to be treated. Even more preferably, the FMA is capable of reducing the Hardness of a fecal analog or actual feces by about 25% (and preferably about 50%) at a concentration of no more than about 5 weight percent of the feces to be treated. In other preferred embodiments, the FMA is capable of reducing the Hardness of a fecal analog or actual feces by 25% (and preferably about 50%) at a concentration of no more than about 1 weight percent of the feces to be treated. In yet other preferred embodiments, the FMA is capable of reducing the Hardness of a fecal analog or actual feces by about 25% (and preferably about 50%) at a concentration of no more than about 0.5 weight percent of the feces to be treated. Typically, the the FMA is capable of reducing the Hardness of a fecal analog or actual feces by about 25% (and preferably about 50%) at a concentration of between about 0.1 and about 10 weight percent of the feces to be treated.

Preferably, the defined reduction in Hardness is effected within the range of between about 30 minutes, more preferably within about 15 minutes, even more preferably within about 5 minutes, even more preferably within about 3 minutes, and most preferably in about 1 minute after contact with the feces. Typically, the desired Hardness change is effected within the range of about 1 minute to about 10 minutes. In more preferred embodiments, the defined decrease in Hardness is effected within about 3 minutes at an FMA concentration of no more than about 5% by weight of the feces to be treated or within 3 minutes at an FMA concentration of about 1.5% by weight of the feces to be treated. In other preferred embodiments, the FMA is capable of reducing the Hardness of a fecal analog, or actual feces, by about 50% within about 3 minutes at a concentration of no more than about 5%.

The reference Hardness values of two synthetic fecal analog materials are presented in Table I. (Hardness has been found to be closely related to the complex modulus of feces.) Analog A represents the water content, Hardness, and adhesion properties of typical "runny" feces, while Analog B represents typical "pasty" feces. Two consistencies of feces are simulated so as to better illustrate the activity of the FMAs. The methods of preparing Analogs A and B are described in the Test Methods section below.

TABLE I

| Fecal Analog | Fecal Analog Hardness (g) |
|---|---|
| A | 8.6 |
| B | 620 |

Fecal analogs A and B provide a robust and repeatable means to evaluate FMA performance. However, actual feces is a very complex material. For certain chemical treatments, the FMA effect may be greater for actual feces than for either of the analogs described above. For one of the agents evaluated, Hardness data is presented in terms of hardness change for feces analogs and actual feces, in order to demonstrate the similarity in relative responses to the treatment. The actual feces used in these experiments consisted of a composite "runny" feces. The composite runny feces sample was pooled using several bowel movements (uncontaminated by urine) produced by two U.S. breast-fed, four month old, male infants. Feces pooling was accomplished via a Seward Stomacher 400 Lab System by Seward Medical, Ltd. of London, UK. For reference, the Hardness of the untreated (i.e., as collected) pooled runny feces sample was 28 grams.

The effect of mixing several comparative examples with fecal analogs are illustrated in Table II below. All comparative materials were mixed with the fecal analog as described below in the Sample Preparation Method. As is evident in the data above, the desired changes in Hardness were not achieved by the comparative materials.

TABLE II

| Fecal Analog | Comparative Additive | Concentration (wt. %) | Treated Fecal Analog Hardness (g) |
|---|---|---|---|
| A | Corn Starch (Dietary Fiber Control, Sigma Chemical Co., St. Louis, MO, S-2388) | 1.0<br>5.0 | 12.6<br>8.6 |
| A | Pure Corn Starch Baby Powder (Johnson & Johnson, Co., Skillman, NJ) | 1.0<br>5.0 | 14.4<br>7.1 |
| A | Baby Powder (talc) (Johnson & Johnson, Co.) | 1.15 | 10.2 |
| B | Corn Starch (Dietary Fiber Control, Sigma Chemical Co., St. Louis, MO, S-2388) | 1.1<br>4.9 | 643<br>533 |
| B | Baby Powder (talc) (Johnson & Johnson, Co.) | 1.0<br>5.0 | 854<br>679 |

The feces modifying agent of the present invention may include one or more "water liberating" agents capable of separating the liquid portion of the feces (i.e., water) from the solid structure of the feces and/or reducing the degree of "binding" of the feces water to the solid feces components. Without wishing to be bound by theory, it is believed that feces comprises water in several states. For example, the feces includes free water, bound water (bound water may be held in a "colloidal" structure via an electrical double layer on the surface of the particles, organized in a polymeric "gel" structure, or associated with other charged elements in the fecal matrix), and entrapped water (e.g., inside bacteria). It is also believed that the solid and polymeric components of the feces act to organize bound water into higher energy states (i.e., more energy is required to separate the water from the matrix) as compared to free water or "unbound" water. (The solid components of feces (soluble and insoluble) generally include one or more of the following; undigested food material (e.g., fiber), bacteria, mucins in the form of macromolecular glycoproteins, long chain polysaccharides, fats, soaps, protein globules, and the like.) It is believed that mucins are a primary contributor to the structure (i.e., water-holding capacity, viscosity, and elasticity) of low viscosity feces such as runny bowel movements. It is further believed that the long distance effects of the mucins are significantly enhanced by polymerization of the glycoproteins by crosslinking via disulfide bonds. The water content of viscous bodily wastes such as fecal material is relatively high, generally greater than 50%, and often between about 60% and about 95% by weight. However, conventional absorbent articles are incapable of separating much of the water from the fecal matrix or significantly disrupting the fecal matrix. (As used herein, the term "fecal matrix" refers to the feces as a whole, including any solid or soluble components such as biopolymers.) Thus, very little of the feces (generally only a portion of the free water) is actually absorbed such that it can be adequately contained.

In order to improve the efficacy of the absorbent structure with regard to feces, the FMAs of the present invention may include "water liberating" agents which act to separate the bound and/or entrapped from the fecal matrix water and/or disrupt the fecal matrix structure, thereby increasing the relative amount of the feces which may penetrate an absorbent structure. "Liberated water" in feces or analogs may remain within the feces mass resulting in reduced feces viscosity, or completely separate from feces, forming two distinct phases, water and the remaining feces. If the water is completely separated, the remaining feces (i.e., non-water phase) becomes significantly harder. In the absence of absorbent materials in contact with the feces, liberation of water from the fecal matrix decreases the viscosity of the overall fecal mass by permitting the liquid portion of the fecal matter to flow more freely. The feces's decrease in viscosity promotes its penetration into an acceptance element or absorbent structure. Greater penetration of the absorbent structure, in turn, increases the likelihood that the absorbent article will be able to store and/or immobilize the waste away from the wearer's skin. Accordingly, the absorbent article's overall performance may be significantly improved.

Liberation of water may be caused by the destabilization of the colloidal or gel nature of the feces and preferably decreases the viscosity of the feces and increases the ability of the feces to flow into the absorbent structure, and may also enhance the ability of any absorbent materials in contact with the treated feces to dewater and immobilize the feces. However, in some embodiments it may be undesirable to have immobilization occur on the surface of the absorbent structure because the solid fraction of the feces may still be accessible to the user. Thus, it maybe preferred to limit the contact of feces with absorbent media until the feces has penetrated the structure to the desired depth or location for immobilization away from the user. In such embodiments, the feces viscosity is preferably decreased while on the surface of, or prior to contact with, the absorbent structure, and dewatered and/or immobilized once it has sufficiently penetrated the structure.

Feces Modifying Agents which act to decrease the viscosity of feces as described above include, but are not limited to, reducing agents. For example, agents that reduce disulfide bonds (—S—S-bonds) as found in colonic mucous (colonic mucous generally comprises macromolecular glycoproteins linked by disulfide bonds) can effect a significant viscosity reduction in feces having high mucous content. While not wishing to be bound by theory, it is believed that reduction of the mucin disulfide bonds (which function as crosslinks between mucin polymer chains) significantly reduces the average molecular weight of the glycoprotein structure in feces such as runny feces to a level well below the "gel point" of the mucin (i.e., long-distance structure becomes impossible due to the relatively small size of the glycoproteins). Exemplary reducing agents include sulfites such as sodium hydrogensulphite, sodium sulfite and sodium dithionite, thiols and thiol alcohols (e.g., 2-mercaptoethanol, dithiothreitol, and dithioerythritol), mercaptoacetic acid, sodium thioglycolate, thiolactic acid, thioglycoamide, glycerol monothioglycolate, borohydrides (e.g., sodium borohydride), tertiary amines, thiocyanates such as sodium thiocyanate, thiosulfates such as sodium thiosulfate, cyanides such as sodium cyanide, thiophosphates such as sodium thiophosphate, arsenites such as sodium arsenite, phosphines such as triphenyl phosphine, phenols such as thiophenol and p-nitrophenol, betaines, and others including, but not limited to, lithium aluminumhydride, aluminum chloride, guanidine hydrochloride, stannous chloride, hydroxylamine, and $LiHB(C_2H_5)_3$.

Viscosity reduction performance of a representative reducing agent (mixed with a fecal analog and actual feces as described in the Sample Preparation Method in the Test Methods section below) is illustrated in the data in Table III.

TABLE III

| Feces/<br>Fecal<br>Analog | Reducing Agent | Concentration (wt. %) | Treated Feces/Fecal Analog Hardness (g) | % Change in Hardness |
|---|---|---|---|---|
| Composite Runny Feces Sample | sodium hydrogensulfite (Aldrich Chemical Co., Milwaukee, WI cat.# 24,397-3) | 5.0 | 10.1 | (50) * |
| B | sodium hydrogensulfite (see above) | 5.0 | 311⁻ | (64) |

* ( ) indicates decrease in the value.

Any of the reducing agents described above may be used to enhance the ease of feces penetration into an absorbent structure by liberating water from the feces solid matrix by reducing the macromolecular gel character of the feces, thereby decreasing the viscosity of the feces prior to contact with absorbent media.

While in certain embodiments it is desirable to treat the entire mass of feces within the article (i.e., "bulk" treatment), in some preferred embodiments only a portion of the feces is treated with the FMA. This may be preferable from an FMA utilization standpoint or to eliminate the need for mixing of the FMA into the fecal mass. For example, it may be suitable to treat only the feces at the skin/feces interface (e.g., to reduce adhesion and/or promote cleaning or reduce spreading across the wearer's skin or to promote absorption or to reduce spreading within the article). Thus, to treat a 1 millimeter thick layer of a fecal mass over a 30 square cm area of the skin or article topsheet at a 10 weight percent level, 0.30 grams of the FMA must be available to the feces in the region of contact with the feces (assuming the specific gravity of the feces is 1.0).

In various embodiments, the FMA may be organic or inorganic, a low molecular weight molecule or polymeric in nature, and/or may be a liquid, solid (e.g., powder, fiber, film, web), or a semi-solid, or combinations thereof The FMA may be presented in a water/oil or oil/water emulsion, a suspension, or mixture. The FMA may be disposed in the article as an individual discrete element (e.g., as a fibrous batt or layer within or attached to the article) or may be held in or on a carrier vehicle, such as a lotion or skin care composition (described below), a web, or may be releasably encapsulated in a packet, cell, or envelope structure.

In embodiments wherein the FMA is delivered via a skin care composition, it may be soluble in the skin care composition or may be held in suspension or as a simple mixture. Larger FMA particles (e.g., preferably greater than about 250 microns in largest dimension) may be at least partially embedded in or held adhesively by the skin care composition. Some exemplary materials useful in the skin care compositions which may be used in embodiments of the present invention include Category I actives as defined by the U.S. Federal Food and Drug Administration's (FDA) Tentative Final Monograph on Skin Protectant Drug Products for Over-the-Counter Human Use, which presently include: alantoin, aluminum hydroxide gel, calamine, cocoa butter, dimethicone, cod liver oil (in combination), glycerine, kaolin, petrolatum, lanolin, mineral oil, shark liver oil, white petrolatum, talc, topical starch, zinc acetate, zinc carbonate, zinc oxide, and the like. Other potentially useful materials are Category III actives as defined by the U.S. Federal Food and Drug Administration's Tentative Final Monograph on Skin Protectant Drug Products for Over-the-Counter Human Use tentative final monograph on skin protectant drug products for over-the-counter human use, which presently include: live yeast cell derivatives, aldioxa, aluminum acetate, microporous cellulose, cholecalciferol, colloidal oatmeal, cysteine hydrochloride, dexpanthanol, Peruvian balsam oil, protein hydrolysates, racemethionine, sodium bicarbonate, Vitamin A, and the like. Many of the FDA monographed skin care ingredients are currently utilized in commercially available skin care products, such as A and D® Ointment, VASELINE® Petroleum Jelly, DESITIN® Diaper Rash Ointment and Daily Care Ointment, GOLD BOND® Medicated Baby Powder, AQUAPHOR® Healing Ointment, BABY MAGIC® Baby Lotion, JOHNSON'S ULTRA SENSITIVE® Baby Cream, Johnson's baby lotion, lip balms, etc. Other suitable skin care compositions are described in detail in U.S. Pat. Nos. 5,643,588, 5,607,760, 5,609,587, and 5,635,191. The disclosures of each of these patents is incorporated herein by reference.

The skin care compositions useful in the present invention preferably have a melting profile such that they are relatively immobile and localized on the wearer-contacting surface of the article at room temperature, are readily transferable to the wearer at body temperature, and yet are not completely liquid under extreme storage conditions. Preferably, the compositions are easily transferable to the skin by way of normal contact, wearer motion, and/or body heat.

In preferred embodiments, the skin care compositions useful herein are solid, or more often semi-solid, at 20° C., i.e. at ambient temperatures. By "semisolid" is meant that the composition has a rheology typical of pseudoplastic or plastic liquids. When no shear is applied, the compositions can have the appearance of a semi-solid but can be made to flow as the shear rate is increased. This is due to the fact that, while the compositions may contain primarily solid components, they may also include some minor liquid components. Preferably, the compositions of the present invention have a zero shear viscosity between about $1.0 \times 10^6$ centipoise and about $1.0 \times 10^8$ centipose. More preferably, the zero shear viscosity is between about $5.0 \times 10^6$ centipoise and about $5.0 \times 10^7$ centipoise. As used herein the term "zero shear viscosity" refers to a viscosity measured at very low shear rates (e.g., 1/sec) using plate and cone viscometer (a suitable instrument is available from TA Instruments of New Castle, Del. as model number CSL 100). One of skill in the art would recognize that using means other than high melting point components can be used to provide comparable viscosities. For example, the lotion could be provided with a structure which has a high zero shear viscosity but, on the application of shear, such structure collapses with a resulting viscosity reduction (Compositions of this type are said to have a yield value.) Such structure can be provided by certain clay materials, such as bentonite clays or montmorillonite clays, and by fumed silica. Particularly preferred are the fumed silicas as are available from the Cabot Corp., Cab-O-Sil Div. Of Tuscola, Ill. as CAB-O-SIL. A skilled person would also recognize that the zero shear viscosity of such compositions may be measured by extrapolating a plot of viscosity vs. shear rate to a shear rate of zero. Such viscosity measurements should be conducted at a temperature of about 20° C.

The skin care composition carrier vehicle may include a useful active ingredient such as one or more skin protectants or emollients. As used herein, the term "emollient" refers to a material that protects against wetness or irritation, softens, soothes, supples, coats, lubricates, moisturizes, protects and/or cleanses the skin. (It will be recognized that several of the monographed actives listed above are "emollients", as that term is used herein.) In a preferred embodiment, emollients will have either a plastic or liquid consistency at ambient temperatures, i.e., about 20° C. Such a consistency allows the composition to impart a soft, lubricious, lotion-like feel.

Representative emollients useful in the present invention include, but are not limited to, emollients that are petroleum-based; sucrose ester fatty acids; polyethylene glycol and derivatives thereof; humectants; fatty acid ester type; alkyl ethoxylate type; fatty acid ester ethoxylates; fatty alcohol type; polysiloxane type; propylene glycol and derivatives thereof; glycerine and derivatives thereof, including glyceride, acetoglycerides, and ethoxylated glycerides of $C_{12}-C_{28}$ fatty acids; triethylene glycol and derivatives thereof, spermaceti or other waxes; fatty acids; fatty alcohol ethers, particularly those having from 12 to 28 carbon atoms in their fatty chain, such as stearic acid; propoxylated fatty alcohols; other fatty esters of polyhydroxy alcohols; lanolin and its derivatives; kaolin and its derivatives; any of the monographed skin care agents listed above; or mixtures of these emollients.

Another preferred component of the skin care composition carrier vehicles useful in the present invention is an agent capable of immobilizing the composition (including the preferred emollient and/or other skin conditioning, therapeutic, or protective agents and/or the FMA(s) present in the composition) in the desired location in or on the treated article. The immobilizing agent may counteract the tendency of an emollient to migrate or flow by keeping the emollient primarily localized on the surface or in the region of the article to which the composition is applied. This is believed to be due, in part, to the fact that the immobilizing agent raises the melting point and/or viscosity of the composition above that of the emollient. Since the immobilizing agent is preferably miscible with the emollient (or solubilized in the emollient with the aid of an appropriate emulsifier or dispersed therein), it entraps the emollient on the surface of the article's wearer contacting surface or in the region to which it is applied.

It is also advantageous to "lock" the immobilizing agent on the wearer contacting surface or the region of the article to which it is applied. This can be accomplished by using immobilizing agents which quickly set up (i.e., solidify) upon application to the article. In addition, outside cooling of the treated article via blowers, fans, cold rolls, etc. can speed up crystallization of the immobilizing agent.

In addition to being miscible with (or solubilized in) the emollient, the immobilizing agent preferably has a melting profile that provides a composition that is solid or semisolid at ambient temperature. In this regard, preferred immobilizing agents have a melting point of at least about 35° C. This prevents the immobilizing agent from having a tendency to migrate or flow. Preferred immobilizing agents will have melting points of at least about 40° C., and more typically in the range of from about 50° to about 150° C.

Immobilizing agents suitable for use in the present invention can be selected from any of a number of agents, so long as the preferred properties of the skin care composition provide the skin benefits described herein. Preferred immobilizing agents generally comprise a member selected from the group consisting of $C_{14}-C_{22}$ fatty alcohols, $C_{12}-C_{22}$ fatty acids, and $C_{12}-C_{22}$ fatty alcohol ethoxylates having an average degree of ethoxylation ranging from 2 to about 30, and mixtures thereof Preferred immobilizing agents include $C_{16}-C_{18}$ fatty alcohols, preferably crystalline high melting materials selected from the group consisting of cetyl alcohol, stearyl alcohol, behenyl alcohol, and mixtures thereof. (The linear structure of these materials can speed up solidification on the treated absorbent article.) Other preferred immobilizing agents include $C_{16}$–$C_{18}$ fatty acids, preferably selected from the group consisting of palmitic acid, stearic acid, and mixtures thereof. Mixtures of palmitic acid and stearic acid are particularly preferred. Still other preferred immobilizing agents include $C_{16}$–$C_{18}$ fatty alcohol ethoxylates having an average degree of ethoxylation ranging from about 5 to about 20. Preferably, the fatty alcohols, fatty acids and fatty alcohols are linear. Importantly, these preferred immobilizing agents such as the $C_{16}$–$C_{18}$ fatty alcohols increase the rate of crystallization of the composition causing the composition to crystallize rapidly onto the surface of the substrate. Yet other types of ingredients suitable for use as immobilizing agents, either alone, or in combination with the above-mentioned immobilizing agents, include waxes such as carnauba, ozokerite, beeswax, candelilla, paraffin, ceresin, esparto, ouricuri, rezowax, isoparaffin, and other known mined and mineral waxes.

The Feces Modifying Agent may be delivered to the feces directly via transfer of the FMA to the feces or it may initially transfer to the wearer's skin or other element of the article prior to transfer to the feces. The carrier vehicle may be integral with the disposable article or may constitute, or be component of, a separate article to be applied to the wearer (preferably at least over the perianal region) prior to, or in place of, a diaper, training pant, underwear, or other article.

The means for joining the FMA to a carrier vehicle may include any means known in the art, such as adhesives (particularly water soluble adhesives), hydrogen bonding, releasable encapsulation, spraying, coating, and the like. Hydrogen bonding of the FMA to a substrate may be effected by slightly wetting either the FMA or at least a portion of the substrate with water. Upon drying, the FMA is releasably affixed to the substrate (i.e., subsequent contact with liquid water will break the bond). This effect is enhanced for those FMAs which "gel" and become sticky when wet (e.g., alginic acid and derivatives, etc.). Wetting may be accomplished by subjecting either the FMA, substrate, or both to a high humidity environment (e.g., 80% RH or greater) prior to or at the time of contact. Alternatively, water may be sprayed, misted, or atomized over at least a portion of either the agent or substrates prior to or at the time of their contact. In such cases, the structure is preferably dried prior to incorporation into an article.

In other preferred embodiments, the FMA may be associated with a gasket such as a leg cuff, waist barrier, waistband, waste pocket or with a feces spacing element. In embodiments wherein the FMA is associated with a gasketing element such as a leg cuff, waist barrier, or waist pocket, it is preferred that the FMA be associated with the portion of the gasket disposed closest to the exit point of the waste from the wearer (e.g., the anus for feces). In certain preferred embodiments, the FMA is releasably attached to the surface of the gasket material so as to promote treatment of the feces contacting the gasket. The FMA may be releasably attached to the gasket surface via any of the means described above or any other means known in the art. In other embodiments, the FMA is releasably encapsulated at or near at least a portion of the gasket surface. In embodiments including feces spacing elements, any portion of the spacing element may comprise one or more FMAs. The spacing element may be releasably coated with the agent as described above or may comprise cells, packets, or pouches of the agent covered, at least in part, with a water or feces-soluble film (as described above).

The FMA may contact the feces at or near the surface of the article (e.g., at the topsheet/feces interface), within the article (as in a waste management element 120 as described below), or at the body-side surface of the fecal mass (i.e., having first been transferred to the skin or other surface above the plane of the article). Typically, the FMA will contact the feces in the region of the article associated with the wearer's anus (e.g., crotch region in a diaper context). The feces may alternatively contact the FMA as it passes through an orifice, flange, valve, or the like, at or near the anus of the wearer. In such cases, the FMA may be expressed or drawn from the orifice or valve (e.g., from reservoirs) by the pressure of the passage of the feces as it extrudes from the body. The orifice may comprise a slit, slot, or perforation in a sheet, envelope, packet or other structure containing the FMA or composition comprising a FMA disposed in proximity to the exit point of the feces from the body. The orifice may be initially sealed by soluble film that is dissolved by contact with the feces, releasing the agent or composition. Alternatively, the orifice may be opened as the structure is deformed by passage or pressure of the feces. The feces pressure, in addition to body pressure and movement may aid in the expression of FMA through the orifice to the feces.

The FMA may be delivered passively (e.g., the feces flows and contacts it during normal wearing conditions), actively (e.g., an element in the article responds to a signal and delivers/releases the FMA to the feces), or via a secondary carrier (e.g., a powder or other skin care composition initially transferred to the wearer's skin). Delivery of the FMA to the feces may occur as a result of feces extrusion pressure, weight, temperature, enzyme activity, water content, and/or pH; urine presence (e.g., urine triggering release of the agent in response to or in anticipation of a defecation); body motions, pressure, or heat; or any other trigger or event during the wear cycle of the article.

The FMA may be initially stored within or on the article or any portion thereof and subsequently released by any of the triggering events described herein. In certain preferred embodiments, the FMA is releasably encapsulated under a film, in cells, packets, envelopes and the like so as to prevent migration and/or loss of the agent prior to the article being insulted by feces and/or to aid in positioning the FMA for contact with the feces during use. The film covering, cells, packets, or other "containers" for the agent may comprise a water-soluble film over at least the feces-contacting surface area of the container. The water from urine, feces, or other feces dissolves the film releasing the agent (i.e., triggering release) to contact and treat the feces. An example of a water soluble film useful in the present invention is a polyvinyl alcohol film available as MONOSOL M7031 from Chris Craft Industrial products of South Holland, Ill. or HL1636 from the H.B. Fuller Co. of St. Paul, Minn. Alternatively, the film may be soluble only in the presence of certain fecal enzymes (like trypsin) or in certain pH ranges.

The release of the agent may be rapid (such as with an explosive gas release created by contacting urine or fecal water with a gas-evolving composition) to embed or coat the feces with the agent. The gas evolving composition may comprise particles, globules, etc. of one or more substances which evolve gas when mixed with or together in water (e.g., sodium bicarbonate or sodium bicarbonate and citric acid). The particles may be embedded in a water soluble matrix (e.g., PVA). The FMA may be disposed on or attached to the waste contacting surface of the film or may be embedded in the water soluble film between the gas-evolving composition and the feces contacting surface. Thus, for example, when water present in the feces dissolves the water-soluble film, the gas-evolving composition is activated (i.e., the component(s) mix with the water) and gas is evolved rapidly, forcing mixing of the FMA and the feces. The particles may comprise combinations such as citric acid and sodium bicarbonate which, when mixed with water, rapidly releases carbon dioxide gas. Alternatively, the gas-evolving composition may comprise water soluble capsules containing compressed gas and the FMA. Water from the feces which contacts the capsules can act to dissolve the film and release the gas explosively, again forcing mixing/embedding of the agent in the feces. Other compositions and gas-evolving or releasing systems are contemplated and are included in the scope of this invention.

Figure 8:
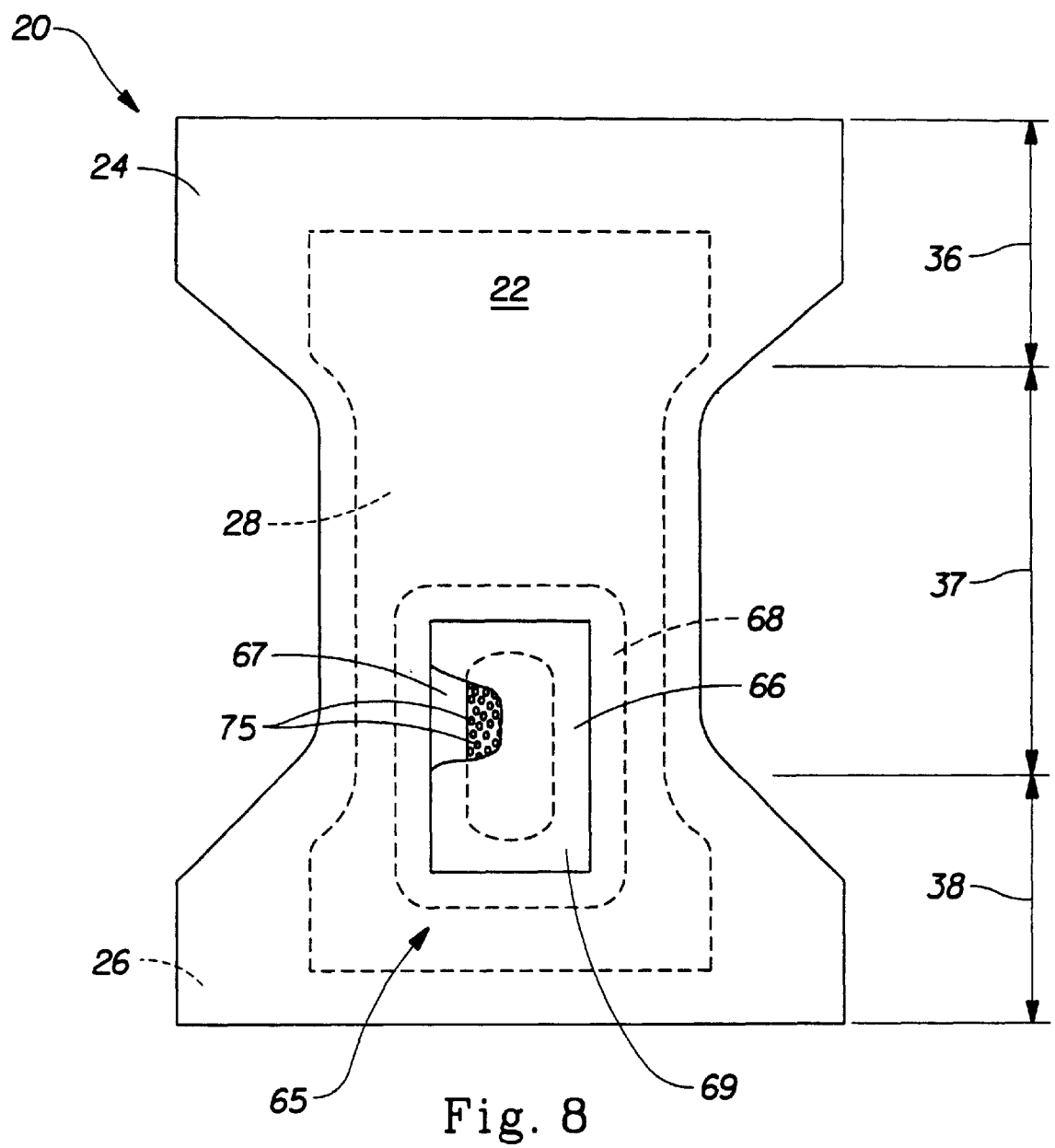
FIG. 8 is a plan view of an absorbent article embodiment of the present invention having portions cut away to reveal the underlying structure, the body-facing surface of the diaper facing the viewer.

The article of the present invention may also include a responsive system 65 comprising a sensor 66, actuator 67, and stored energy employed to transport the FMA to the feces, mix the agent with the feces, or cause the agent to be expressed to contact the feces. One preferred embodiment comprises a shaped, compressed, macro-porous foam 68 held in compression under a water-soluble polyvinyl alcohol film as shown in FIG. 8. The foam 68 additionally comprises an FMA 75. Contact with fecal water results in dissolution of at least a portion of the PVA film resulting in a release of the stored mechanical energy in the foam and mechanical transport of the agent toward and into the fecal mass. In certain embodiments, mixing may occur via a mechanism incorporated in the article as described above (e.g., responsive system), mechanical action from the wearer's weight and/or motion, and/or the flow of feces during or subsequent to the act of defecation (especially low viscosity feces) to facilitate treatment of a greater proportion of the fecal mass. Other suitable responsive systems are described in more detail in co-pending U.S. patent applications Ser. No. 09/106,/424 entitled "Disposable Article Having A Discontinuous Responsive System" filed in the names of Roe, et al. on Jun. 29, 1998 now U.S. Pat No. 6,160,198 issued Dec. 17, 2000, which is incorporated by reference herein.

Figure 6:
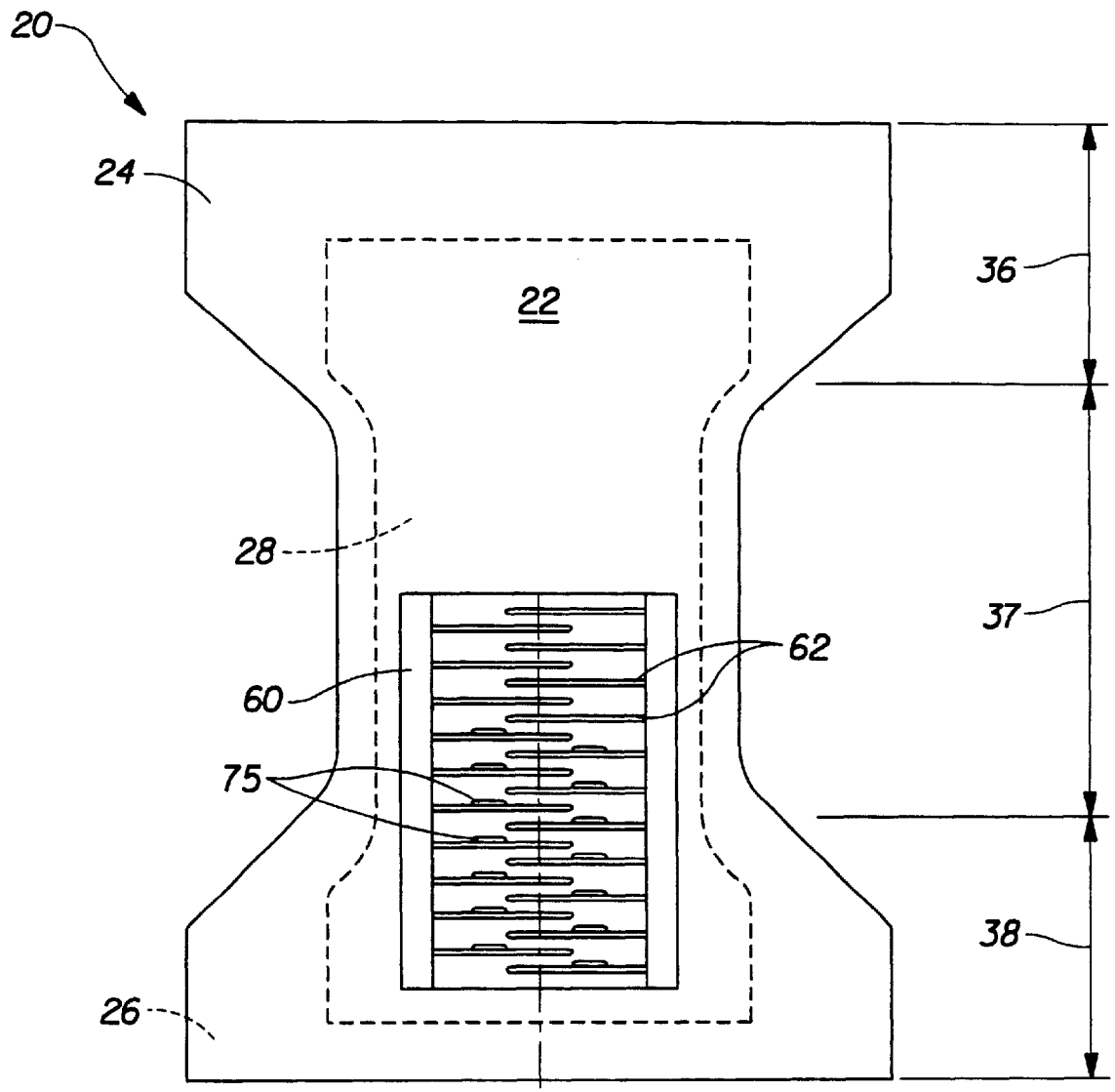
FIG. 6 is a plan view of an alternative embodiment of the present invention.
Figure 7:
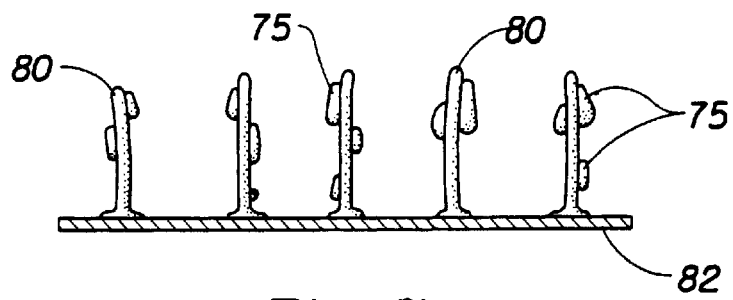
FIG. 7 is an enlarged cross sectional view of an embodiment of the present invention.

In alternative embodiments, the FMA may be disposed on or associated with three-dimensional structures joined to or separate from other elements of the absorbent article. For example, the absorbent article may include an element with protrusions, bumps, loops or the like which help make the FMA available to contact the feces. In one preferred embodiment, "hairs" or strands of a hot melt resin including the feces modifying agent may be printed on a substrate 82. (An example of a substrate including hairs 80 comprising a feces modifying agent are shown in FIG. 7.) The agent may be incorporated into the resin such that it moves to the surface of the hairs and is available to the feces. Alternatively, the agent may be releasably bonded to the hairs via any of the techniques described above. Examples of suitable hairs and hooks are described in more detail in U.S. Pat. No. 5,058,247 issued to Thomas et al. on Oct. 22, 1991; U.S. Pat. No. 5,116,563 issued to Thomas et al. on May 26, 1992; U.S. Pat. No. 5,326,415 issued to Thomas et al. on Jul. 5, 1994; and U.S. Pat. No. 5,762,645 issued to Peck et al. on Jun. 9, 1998. Each of these patents is incorporated by reference herein In yet another embodiment, the FMA may be delivered to the feces via a brush structure, one example of which is shown in FIG. 6. A brush structure 60 may include a multiplicity of substantially aligned strands, fibers, twisted yarns, strings, or other filamentous materials affixed to a substrate. The substrate may be planar, curved, ribbon-like, or have compound curvature and may be porous or non-porous. The brush filaments 62 are preferably bendable under the forces exerted by the feces during excretion so as to allow feces to readily pass through or between the filaments 62. The brush filaments 62 may be permanently or releasably affixed to the substrate. The filaments 62 may be of plant or animal origin (e.g., cotton, etc.), cellulosic or synthetic and may have different or similar lengths. The FMA is releasably affixed to the filaments 62 of the brush structure 60 such that as the feces is pushed past the brush filaments 62, the agent is released and mixed with the feces. The brush structure 60 may be integral with the article or may be separately applied to the wearer's perianal region and may optionally comprise an adhesive or other joining means for adhering the structure to the wearer or the article. The brush structure 60 may be mounted over a spacer (as described above) having a void under the filaments 62 so as to provide a space for the treated feces to occupy.

The FMAs may also be delivered via the use of "smart" gels that undergo a phase transition or a geometric or volume change in response to certain changes in pH, water content and/or some other trigger. Shape memory materials (i.e., metal alloys or plastics that return to a pre-set geometry or shape when the temperature reaches a pre-determined threshold) may also be employed to move the agent into position to contact or mix with feces, given the appropriate temperature change. Additionally, swellable materials, such as superabsorbent polymers or foams, may be used to promote feces contact with the FMA. As a structure containing such swellable materials imbibes water, whether from feces or urine, it may transport a FMA associated with the body-facing surface of the structure toward a fecal mass and/or promote mixing with the feces. Foam-forming materials may also transport the FMA and promote contact with feces in the article. In this case, the foam forming material comprises the FMA (or is associated with the agent) and coats the fecal mass as the foam is generated and its volume increases.

The FMAs may also be held on or within macro-particulate elements, as described below. These macro-particulate elements may be contained in a waste management element 120, attached to a topsheet, cuff, or other feature of the article (releasably or not), or loose in a separate article attached independently to the body. (Some exemplary macro-particulate structures are shown in FIGS. 2–4.) Further, any of the structures that hold, carry, deliver, or mix the FMA may comprise protrusions or other three-dimensional geometries designed to increase contact area of the FMA and the feces and/or to promote mixing.

In preferred embodiments, the FMA is associated with the topsheet of the absorbent structure or article. However, the FMA may be associated with a layer underneath the topsheet, such as an acquisition layer. In embodiments where the FMA is disposed in a sublayer underneath a topsheet in a waste management element 120, as described below, feces must readily penetrate the topsheet, sublayer, and any other overlying structure for the agent to be available. Thus, it is preferred that such structures have an Acceptance Under Pressure of at least about 0.50 g/cm2/J, and preferably at least about 1.0 g/cm2/J as described in the Test Methods section below. In any case the agent is preferably located near the region of the article generally associated with the wearer's perianal region.

As shown in FIG. 2, the present invention may include a waste management element 120. The waste management element 120 is designed to help manage the acceptance, storage and/or immobilization of the viscous fluid bodily waste. The waste management element 120 can be located anywhere in the article, including the crotch region or either waist region, or may be associated with or be included in any structure or element such as the core 28, a leg cuff, etc. In preferred embodiments, the waste management element 120 is located in the region of the article that is near the wearer's perianal region when worn. This helps ensure that any waste discharged is deposited on or near the waste management element 120.

Although structures which accept, store and immobilize viscous fluid bodily wastes are preferred, in certain embodiments of the present invention, the waste management element 120 may comprise only an acceptance element, a storage element or an immobilization element, or may include a combination of two of the elements, but not the third. Also, in certain embodiments, one element may perform more than one function (e.g., a storage element may perform both the storage and immobilization functions). For example, the absorbent article of the present invention may include an acceptance and a storage element to manage viscous fluid bodily wastes without a separate immobilization element, per se.

The acceptance element 150 may be any material or structure capable of accepting bodily exudates. (As used herein, the term "accept" or "acceptance" refers to the penetration of a structure by materials deposited thereon. Penetration is defined by the passage of materials through the surface of the structure upon which the material was deposited. Penetration of nonuniform structures can be defined as the passage of a material through a plane defining the surface upon which the material was deposited.) The acceptance element 150 may include a single material or a number of materials operatively associated with each other. Further, the acceptance element 150 may be integral with another element of the diaper 20 or may be one or more separate elements joined directly or indirectly with one or more elements of the diaper 20. Further, any or all of the acceptance element 150 may be removable from the absorbent article for separate disposal, if desirable.

The acceptance element 150 is preferably disposed at least partially in the crotch region 37 of the diaper 20 adjacent the body surface 47 of the core 28, although in some alternate embodiments, the acceptance element 150 may include at least a portion of a leg cuff, waistband, fecal waste containment pocket, or the like, or may be operatively associated with any such features. Preferably, at least the portion of the acceptance element 150 located in the region of diaper 20 which is near the anus of the wearer during use is unobstructed by overlying layers of structures, such as the topsheet 24. Thus, it may be desirable to cut out a portion of the topsheet 24 in the region of the article intended to be located near the wearer's anus and to provide an acceptance element 150 as the body-side liner in that region. Alternatively, any or all of the topsheet 24 may be made or treated to act as the acceptance element 150. In one embodiment, as shown in FIG. 2, the acceptance element 150 includes at least a portion of the topsheet 24. In other embodiments, the acceptance element 150 may include at least a portion of other elements of the diaper such as the absorbent core 28 or the storage element (described below).

In some embodiments, it may be desirable to provide the diaper 20 with different acceptance capability in different portions of the diaper. This may be accomplished by providing different acceptance elements in the different regions of the diaper 20 or by providing a single acceptance element 150 which has been manufactured or treated to have regions of differing acceptance characteristics. Further, the acceptance element 150 may be elevated above the plane of the body-facing surface of the article so as to be in better control of exuded viscous fluid bodily wastes. In some embodiments, it may even be desirable to have the acceptance element 150 in contact with skin of wearer in proximity of the viscous bodily waste source (e.g., the perianal region).

Suitable materials and structures for use as the acceptance element 150 may be absorbent or nonabsorbent and may include apertured nonwoven webs, apertured films, apertured formed films, scrims, woven webs, scrim, netting, macroporous thin foams, and the like. One particularly preferred material is a woven netting available as a Toy Tub Bag from Dollar Tree Dist., of Norfolk, Va. Further, the acceptance element 150, or any portion thereof, may be coated with a lotion or other known substances to add, enhance or change the performance or other characteristics of the element. For example, the acceptance element 150 may be hydrophobic or hydrophilic or treated to be either.

As described above, the FMA may be associated with the acceptance element preferably in the wearer's perianal region. In certain preferred embodiments, the FMA is releasably attached to the acceptance element by the means described above. In alternative embodiments, the agent is releasably encapsulated in a structure associated with at least a portion of the acceptance element 150. The agent may be released to the feces upon contact with water, heat, or pressure/wearer motion. The agent may alternatively first be transferred to the wearer's skin or another portion of the article (e.g., leg cuff) prior to deposition onto the feces. For example, urine may effect the release of a releasably encapsulated agent or composition. The agent may transfer to the wearer's skin by body contact and/or pressure. Upon subsequent contact with feces, the agent will transfer from the skin to the surface of the feces.

Once viscous bodily waste has penetrated the waste management element 120, it is desirable to store or hold the waste away from the wearer during the remainder of the wearing cycle and away from the caregiver during the changing process. As used herein, the term "store" refers to the physical separation of material deposited in a diaper from the body-facing surface of the article such that the material deposited in the diaper is not immediately in contact with or accessible to the wearer's skin. Adequate storage capacity is essential to reduce the probability of leakage and the area of skin contaminated by viscous bodily waste because viscous bodily waste that has been stored is less likely to be available to the body-facing surface of the structure for leakage and migration within the article.

The storage element 152 may be located anywhere in the diaper 20. However, it is preferred that the storage element 152 be operatively associated with the acceptance element 150 and/or topsheet 24, if any, such that viscous bodily waste accepted by the acceptance element 150 may enter the storage element 152. (Embodiments are contemplated wherein the diaper 20 has no topsheet 24 or acceptance element 150. In such cases, the bodily waste may enter the storage element 152 directly, without passing through any overlying structure.) In any case, it is preferred that the storage element 152 be located in the region of the diaper 20 which is located near the wearer's anus when the diaper 20 is worn. Accordingly, it is preferred that at least a portion of the storage element 152 be disposed in the crotch region 37 of the absorbent article. However, in some alternate embodiments, the storage element 152 may include at least a portion of either waist region, a leg cuff, the waistband, a fecal waste containment pocket, or the like, or may be operatively associated with any such features. Further, the storage element 152 may be elevated above the plane of body-facing surface of the article so as to be in better control of exuded viscous bodily wastes. In some embodiments, it may even be desirable to have the storage element 152 in contact with skin of wearer in proximity of the viscous bodily waste source (e.g., the perianal region).

The storage capability of the storage element 152 may be uniform or may vary throughout the diaper 20. Such variations may be accomplished by employing multiple storage elements 152 in the diaper 20 or by providing a single storage element 152 with regions of different storage properties. Further, any or all of the storage element 152 may be removable from the absorbent article for separate disposal, if desired.

Figure 5:
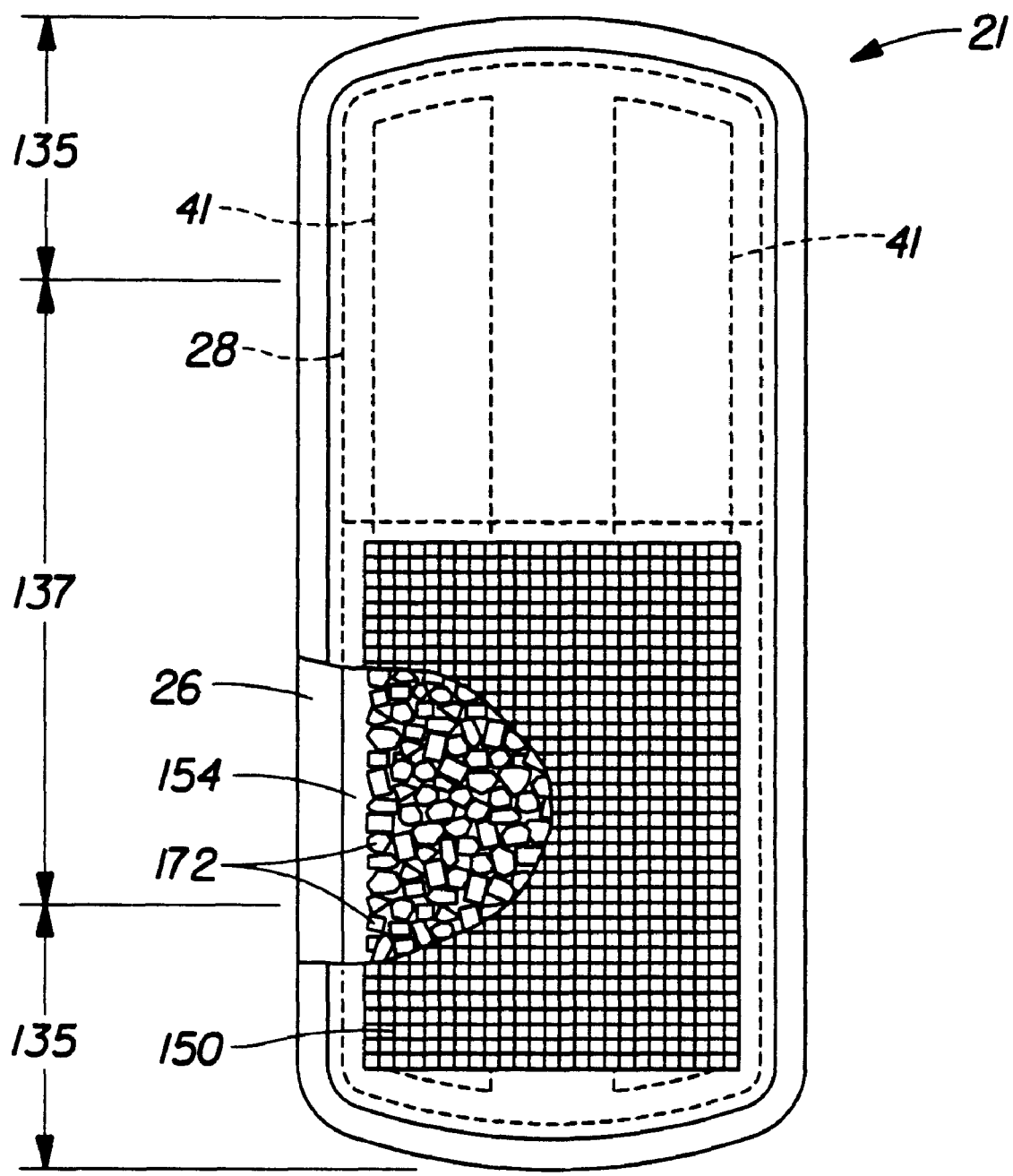
FIG. 5 is a plan view of a sanitary napkin embodiment of the present invention with portions cut away to review the underlying structure.

The storage element 152 may be any material or structure capable of storing bodily exudates, as described above. Thus, the storage element 152 may include a single material or a number of materials operatively associated with each other. Further, the storage element 152 may be integral with another element of the diaper 20 or may be one or more separate elements joined directly or indirectly with one or more elements of the diaper 20. In one embodiment, as shown in FIG. 5, the storage element 152 includes a structure that is separate from the core 28. However, embodiments are contemplated wherein the storage element 152 includes at least a portion of the core 28.

Suitable materials for use as the storage element 152 may include large cell open foams, macro-porous compression resistant nonwoven highlofts, large size particulate forms of open and closed cell foams (macro and/or microporous), highloft nonwovens, polyolefin, polystyrene, polyurethane foams or particles, structures comprising a multiplicity of vertically oriented looped strands of fibers, absorbent core structures described above having punched holes or depressions, and the like. (As used herein, the term "microporous" refers to materials which are capable of transporting fluids by capillary action. The term "macroporous" refers to materials having pores too large to effect capillary transport of fluid, generally having pores greater than about 0.5 mm in diameter and more specifically, having pores greater than about 1.0 mm in diameter.) One embodiment includes a mechanical fastening loop landing element, having an uncompressed thickness of about 1.5 millimeters available as XPL-7124 from the 3M Corporation of Minneapolis, Minn.

Another embodiment includes a 6 denier, crimped and resin-bonded nonwoven highloft having a basis weight of 110 grams per square meter and an uncompressed thickness of 7.9 millimeters which is available from the Glit Company of Wrens, Ga. The storage element 152, or any portion thereof, may include or be coated with a lotion or other known substances to add, enhance or change the performance or other characteristics of the element.

An alternate embodiment of a storage element 152 includes a macro-particulate structure 170 comprising a multiplicity of discrete particles 172, nonlimiting examples of which are shown as FIGS. 2–4. The macro particles 172 preferably have a nominal size, preferably between about 1.0 mm and about 25.4 mm, and more preferably between about 2 mm and about 16 mm. However, particles as small as 0.5 mm and smaller, and particles larger than about 25.4 mm are contemplated. Particles having a nominal size of about 1.0 mm or greater are those which are generally retained on the surface of a U.S. Standard No. 18 mesh sieve screen. Particles having a nominal size of less than about 25.4 mm are those which generally pass through a U.S. Standard 25.4 mm sieve screen. Particles having a nominal size of 16 mm or greater are those which are generally retained on the surface of a U.S. Standard No. 16 mm sieve screen. The nominal particle size is measured prior to incorporating the particles into a storage element 152 for testing or use. Particles having a nominal size of 8 mm or greater are those which are generally retained on the surface of a U.S. Standard 8 mm sieve screen.

The macro-particulate structure 170 may include any number of particles 172. Further, the particles 172 may be unjoined and free to move within the structure 170 or may be joined to each other by any known means. Alternatively, the structure 170 may include an external support, such as a meltblown hot-melt glue, a web, a netting, a scrim, a thread or other adhesive or nonadhesive entangling supports. Any of the particles 172 may also be joined with any other portion of the diaper structure, such as the topsheet or the core. The particles 172 may also be constrained in patterned, three-dimensional regions such as pleats, "pillows", and pockets.

The individual particles 172 may be made from any material suitable for use in absorbent articles, including the materials described above with regard to the absorbent core 28 or the storage element 152. The materials used in the particles 172 may be absorbent, nonabsorbent, microporous, macroporous, resilient, nonresilient, etc. or may have any other desirable characteristic. Examples of macroporous absorbent materials suitable for use in the particles 172 include highloft nonwovens, open cell foams, bundles of fibers, sponges and the like. Other absorbent materials include cellulosic batts, capillary channel fibers, osmotic storage materials such as superabsorbent polymers, etc. Nonabsorbent particles 172 may comprise plastic, metal, ceramic, glass, closed cell foams, column packing materials, synthetic fibers, gels, encapsulated gas, liquids and the like. Further, any or all of the particles 172 may include odor absorbents, lotions, skin care formulations, antimicrobials, pH buffers, enzyme inhibitors, and the like.

The storage element 152 may comprise a single type of particle 172 (size, shape, material, etc.) or may include a mixture of different particles 172. The mixture may be homogeneous; heterogeneous, as when particles 172 having different properties are disposed in certain areas of the storage element 152; layered; or any other desirable configuration. In some embodiments, more than one type of mixture may be employed (e.g., macroporous and nonabsorbent particles 172 may be homogeneously mixed in one layer while another layer includes only absorbent particles.) Different layers of particles may be directly adjacent each other or may be separated by one or more materials, such as netting, scrim, nonwoven or woven webs, film, foam, adhesive, and the like.

The macro-particulate structure 170 preferably includes a continuous interstitial void space 174 that is defined by the space between the particles 172. By varying the size and/or shape of the particles 172, the interstitial void space 174 can be controlled. The particles may be of any known shape, including spheres, oblate spheroids, rectangular and polygonal solids, and the like.

In addition to its storage function, the storage element 152 may transport viscous bodily waste within the absorbent article 20 in directions generally parallel to the plane of the backsheet 26. The transport may be active, such that capillary or other forces result in the movement of the viscous bodily waste or components thereof (e.g., free water). In other embodiments, the transport may be passive whereby viscous fluid bodily waste or components thereof move through the structure under the influence of externally applied forces, such as gravity, wearer pressure or wearer motion. In the case of passive transport, the storage element 152 should have relatively large, interconnected channels, or the like, such that the viscous bodily waste may readily move through the structure with minimum energy input.

The FMA of the present invention may be associated with any portion of the storage element 152, including the macro-particulate structures. In certain preferred embodiments wherein the storage element 152 has raised regions, the FMA is associated with the raised regions of the element. Viscous bodily waste penetrating the acceptance element may contact the FMA and carry it to the "lower" regions of the storage element 152, providing enhanced mixing. For example, the raised tops of loop type storage elements may be slightly wetted or dampened and subsequently contacted with the FMA to releasably affix the FMA to the raised portions, and subsequently dried. The releasable attachment may also be effected via water soluble adhesives. In macro-particulate embodiments, the agent may be held within a macro-porous particle. In alternate embodiments, the agent may be releasably affixed to the exterior surface of the particulate elements. Fecal contact with the FMA preferably effects a release of the agent from the storage element and allows mixing with the feces.

Viscous bodily waste that is accepted by, or penetrates, the absorbent article is preferably also retained in the diaper away from the wearer. One preferred way to retain bodily waste, especially viscous bodily waste, is to immobilize the waste in a location away from the wearer. As used herein, the term "immobilize" refers to the ability of the material or structure to retain stored viscous bodily waste under an applied pressure and/or the influence of gravitational forces.

The immobilization element 154 may be any material or structure capable of reducing the proclivity of viscous bodily waste that has penetrated the immobilization element 154 from leaving the structure. Thus, the immobilization element 154 may include a single material or a number of materials operatively associated with each other. Further, the immobilization element 154 may be integral with another element of the diaper 20 or may be one or more separate elements joined directly or indirectly with one or more elements of the diaper 20. For example, the immobilization element 154 may be an unjoined layer of material disposed under the storage element 152 or may include all or a portion of the storage element 152 which is able to immobilize and retain viscous bodily waste, as described above. In any case, it is preferred that the immobilization element 154 be operatively associated with the storage element 152 and the acceptance element 150. This is necessary to ensure that viscous bodily waste accepted and/or stored by the article passes into or comes in contact with the immobilization element 154. Accordingly, it may be desirable to locate the immobilization element 154 below the storage element 152 and the acceptance element 150, in at least a portion of the crotch region 37 of the article. However, as noted above if the storage element 152 has transportation capabilities, the immobilization element 154 may be located anywhere in the diaper 20 such that the viscous fluid bodily waste accepted and/or stored can be transported to the immobilization element 154. Further, as with the acceptance and storage elements 150 and 152, the diaper 20 may have uniform or nonuniform immobilization capability. Thus, one or more immobilization elements 154 may incorporated in the article having regions of different immobilization and/or retention performance. Further, any or all of the immobilization element 154 may be removable from the absorbent article for separate disposal, if desirable.

Suitable materials for use in the immobilization element 154 include microporous foams, superabsorbent polymer particles or fibers, cellulosic fibers, capillary channel fibers, entangled synthetic fiber batts and the like. Some preferred materials include foam absorbent materials such as those described in U.S. Pat. Nos. 5,260,345; 5,387,207; and 5,625,222. Other preferred materials include absorbent gelling materials such as those described in U.S. Pat. No. 5,147,345 entitled "High Efficiency Absorbent Articles For Incontinence Management" issued to Young et al. on Sep. 15, 1992. Each of these patents is hereby incorporated by reference herein.

The FMA may be associated with the immobilization element 154. In these embodiments, the modifying agent may act to enhance the efficacy and efficiency of the immobilization element 154 by facilitating the removal of water from the feces, and thereby increasing the speed of the immobilization process and/or reducing the final mobility of the remaining solid fraction of feces. The FMA may alternatively serve to increase the viscosity of the feces within the immobilization via a direct thickening mechanism. The FMA may be loosely associated with the immobilization element or may be releasably affixed (i.e., such that feces water may effect its release) to the immobilization element 154.

Preferred Embodiments

As noted above, the present invention is applicable to many types of absorbent articles such as diapers, training pants, incontinence briefs, incontinence undergarments or pads, absorbent inserts, diaper holders and liners, feminine hygiene garments, wipes, disposable mops, bandages and the like and separate articles attached to a wearer over the perianal region. Thus, the following examples of preferred embodiments of the present invention should not construed to limit the scope of the invention.

One preferred embodiment of the present invention is the absorbent article 20 illustrated in FIG. 2. The absorbent article 20 has a first waist region 36, a second waist region 38 and a crotch region 37 located between the first waist region 36 and the second waist region 38. The diaper 20 includes a topsheet 24, a backsheet 26 and an absorbent core 28 disposed between the topsheet 24 and the backsheet 26. The topsheet 24 is disposed in at least a portion of the first waist region 36 adjacent the body facing surface 47 of the core 28 The diaper 20 also includes an acceptance element 150 joined with the topsheet 24 and extending longitudinally away from the topsheet 24 through at least a portion of the crotch region 37 and at least a portion of the second waist region 38. The acceptance element 150 includes a woven netting available as a Tub Toy Bag from Dollar Tree Dist., of Norfolk, Va.

The diaper 20 preferably further includes a storage element 152 located between the acceptance element 150 and the backsheet 26. The storage element 152 is located in at least a portion of the crotch region 37 and at least a portion of the second waist region 38. In this embodiment, the storage element 152 includes a macro-particulate structure 170 comprising particles 172. Specifically, the macro-particulate structure 170 includes about two grams of the scrubber particles mixed with about 0.35 grams of strips of foam absorbent material having a basis weight of 45 grams per square meter, as described in U.S. Pat. No. 5,260,345. (The scrubber particles can be made by cutting the abrasive nonwoven highloft side of a scrubbing pad (e.g., available as Light Duty Scrubbers #00065 from the Libman Company of Arcola, Ill.) into particles of about 8 mm×about 7 mm×about 5 mm.) The strips have dimensions of about 19 millimeters in length, 6.4 millimeters in width, and 2 millimeters in thickness. The scrubber particles are distributed over a 2.5 inch×6.4 inch (16 square inch) area disposed along the longitudinal axis of the article of approximately 0.8 mm thick "thin until wet" foam absorbent material (described in U.S. Pat. No. 5,387,207 which is incorporated herein by reference) having a basis weight of 126 grams per square meter. The scrubber particles are relatively homogeneously mixed with the absorbent foam strips and are free to move within the area circumscribed by the layer of "thin-until-wet" absorbent foam material. The particles and strips are preferably not bonded to the woven netting topsheet or any other layer. A FMA is preferably associated with the particulate elements of the storage layer via any of the means described herein. The acceptance element 150 is bonded to the underlying layers outside the periphery of the layer of "thin-until-wet" absorbent foam.

In another embodiment, as shown in FIG. 5, the absorbent article of the present invention may be an insert 21 or sanitary napkin which is intended to be applied separately to the wearer or to be placed in the wearer's underwear, an outer cover or the like. Thus, the insert 21 is generally not intended to take the form of a pant, but rather is to be used in conjunction with a pant or other structure which holds the insert 21 in place about the wearer. The absorbent insert 21 has a pair of opposed end regions 135 separated by a central region 137 and includes an absorbent assembly 27 which may include an absorbent core 28, an acceptance element 150, a storage element 152 and/or an immobilization element 154. The insert 21 may also include one or more attachment element(s) 41 to hold the insert 21 in place in the pant or outer cover 29 during use. The attachment element 41 may comprise adhesive, cohesive, hooks, snaps, buckles, buttons, ties, magnetic, electronic and/or any other know means for attaching absorbent articles to undergarments.

Test Methods

Viscosity

The viscosity may be determined by a controlled stress rheometer. A suitable rheometer is available from T. A. Instruments, Inc. of New Castle, Del., as model number SC²100. The rheometer utilizes a stainless steel parallel plate fixture. The rheometer has a rigid horizontal first plate onto which the sample is placed and a second plate mounted over the first plate such that the axis of said second plate is perpendicular to the first plate. The second plate is 2 or 4 centimeters in diameter. A two centimeter (2 cm) parallel plate is used for firm, pasty, or highly mucousy samples, while the four centimeter (4 cm) parallel plate is used for very runny or "water-like" fecal samples. The first and second plates are spaced apart up to 2000 microns during the measurement process. The second plate is connected to a drive shaft for axial rotation. The drive motor and strain sensor are also mounted on the drive shaft.

A suitable sample (typically 2 to 3 grams) of an analog to be tested is centered on the first plate and generally centered beneath the axis of the second plate. Prior to the test, any large pieces of undigested food material (e.g., seeds) are removed. The first plate is raised into position. Excess amounts of the sample which are displaced beyond the diameter of the second plate are removed using a spatula. Water is then misted around the edges of the sample to prevent edge effects due to moisture loss during the measurement process. A programmed application of a shear stress, from 50 to 50,000 dynes/cm² for pasty and firm samples, is applied to the sample by the rheometer. For runny and watery samples, a shear stress range of 5 to 5000 dynes/cm² was used instead. The data is fitted to a power law function where the apparent viscosity=$kj^{(n-1)}$, k=consistency (units of cP×sec$^{(n-1)}$), j=shear rate (Units of 1/sec), and n=shear index (dimensionless). Therefore, when j=one 1/sec, the viscosity=k. (The plates are maintained at 35 degrees C. throughout the test.)

Hardness Method

Hardness is measured using a Stevens-Farnell QTS-25 Texture Analyzer, model 7113-5 kg, and associated software on an Intel-based machine having a 486 processor or higher. A ½ inch stainless steel spherical probe and an analog receptacle are provided. A suitable probe is the TA18 probe available from Leonard Farnell Co. of Hatfield, England. The analog receptacle can be made by cutting a 7 milliliter linear low density polyethylene scintillation vial (having an inside diameter of 0.55 inches +/−0.005 inches) to about 16 millimeter length. Suitable vials are available from Kimble Glass Company of Vineland, N.J. as #58503-7 vials. The analog receptacle is filled to the top edge (level) with the analog (Analog A or B, as described below) or feces to be tested. If a modification agent is to be evaluated, the sample is prepared via the Sample Preparation Method described below. The vial is centered under the ½ inch spherical stainless steel probe. The probe is lowered such that it just contacts the surface of the analog in the vial. The probe 162 is moved downward 7 millimeters at about 100 millimeters per minute and then stopped. The Hardness is the maximum recorded resistive force encountered by the probe on its 7 millimeter stroke. (The temperature of the room and the analog should be between about 65 to 75 degrees Fahrenheit during the course of the measurement.) For reference, Hardness has been found to relate strongly to the complex modulus of the material, which is a combination of the viscous and elastic moduli of the material.

Method for Making Analog A 1.5 grams of Ultra Dawn dishwashing liquid (available from the Procter & Gamble Co, Cincinnati, Ohio) is added to an empty metal mixing bowl. 10 grams each of Feclone FPS-2 and Feclone FPS-4 are added into the bowl containing the Dawn. (Both Feclone materials are available from Siliclone Studios, Valley Forge, Pa.) Then 200 milliliters of distilled water heated to 200° F. is added to the mixing bowl. The resultant mixture is then stirred carefully by hand, to avoid introducing air bubbles to the mixture, using a rubber or plastic spatula until homogenous, (usually about 3–5 minutes). If prepared properly, the Analog A will have a Hardness between about 7 and 10 grams as measured by the above Hardness Method.

Method for Making Analog B 5 grams each of Feclone FPS-4, Feclone FPS-6, and Feclone FPS-7 are added into an empty metal mixing bowl. (Both Feclone materials are available from Siliclone Studios, Valley Forge, Pa.). Then 0.67 grams of Carbopol 941 (available from the B.F. Goodrich Corp. of Brecksville, Ohio) is added into the bowl and these four ingredients are stirred until they are homogeneously mixed using a rubber or plastic spatula to ensure adequate dispersion of the powder materials upon mixing in water. Next, 60 milliliters of water heated to 200° F. is added to the mixing bowl The resultant mixture is mixed manually, and is stirred carefully to avoid introducing air bubbles to the mixture, using a rubber or plastic spatula until homogenous (usually about 3–5 minutes). If prepared properly, the Analog A will have a Hardness between about 600 and 650 grams.

Method for Making Analog C

Analog C is a fecal material analog made by mixing 10 grams of Carbopol 941 available from the B.F. Goodrich Corporation of Brecksville, Ohio, or an equivalent acrylic polymer in 900 milliliters of distilled water. The Carpobol 941 and distilled water are weighed and measured separately. A 3-bladed marine-type propeller having a 2 inch diameter paddle, (available from VWR Scientific Products Corp. of Cincinnati, Ohio, Catalog # BR4553-64, affixed to a ⅜" stirring shaft BR4553-52), is used to stir the distilled water. The propeller speed should be constant at 450 rpm during mixing. The mixer should form a vortex without splashing. The Carbopol is slowly sieved into the water so that it is drawn into the vortex and mixed without forming white clumps, or "fish eyes". The mixture is stirred until all of the Carbopol has been added, and then for a period of 2 minutes thereafter. The sides of the bowl containing the mixture should be scraped and the bowl should be rotated as needed to achieve a homogeneous mixture. (The mixture will likely be slightly cloudy with air bubbles). One hundred grams of a 1.0 N volumetric NaOH solution, available from J.T. Baker Co., Phillipsburg, N.J., is then slowly measured into the mixture and the mixture is stirred until homogeneous. The mixture should become thick and clear. The mixture should be stirred for 2 minutes after the addition of the alkali solution. The neutralized mixture should be allowed to equilibrate for at least 12 hours and should be used for the Acceptance Under Pressure test within 96 hours thereafter. Before the Carbopol mixture is used, it should be stirred in the container at low speed (about 50 rpm) for about 1 minute to ensure the mixture is homogeneous.

Analog C should, if prepared correctly, have a "Hardness" value between 55 and 65 grams. Hardness is measured using a Stevens-Farnell QTS-25 Texture Analyzer, model 7113-5 kg, and associated software on an Intel-based machine having a 486 processor or higher. A ½ inch stainless steel spherical probe and an analog receptacle are provided. A suitable probe is the TA18 probe available from Leonard Farnell Co. of Hatfield, England. The analog receptacle can be made by cutting a 7 milliliter linear low density polyethylene scintillation vial (having an inside diameter of 0.55 inches +/−0.005 inches) to a 15 millimeter length. Suitable vials are available from Kimble Glass Company of Vineland, N.J. as #58503-7 vials. The analog receptacle is filled to within 2 millimeters of the top edge with the analog to be tested. The vial is centered under the ½ inch spherical stainless steel probe. The probe is lowered to a distance of about 1 millimeter from the surface of the analog in the vial. The probe 162 is moved downward 7 millimeters at 100 millimeters per minute and then stopped. The Hardness is the maximum recorded resistive force encountered by the probe on its 7 millimeter stroke. (The temperature of the room and the analog should be between about 65 to 75 degrees Fahrenheit during the course of the measurement.)

Sample Preparation Method

A 250 mL Precleaned VWRbrand TraceClean jar (VWR # 15900-196) is placed on a balance and tared. The desired amount of chemical agent is measured into the cup and its exact weight is recorded. After the chemical weight is recorded the balance is tared again. The desired amount of feces or fecal analog is measured into the cup containing the chemical agent. The exact amount of feces or fecal analog is recorded and the chemical agent and feces or fecal analog is stirred vigorously using the spatula end of a Standard Ayre Cervi-Scraper (VWR # 15620-009) until homogeneous (total stirring time is generally about 2 minutes). For the purposes of this method, the beginning of the stirring process is defined as t=0 minutes. After the sample is mixed it is allowed to sit for the remainder of the desired reaction time. For the data presented herein, this reaction time is set at t=three minutes elapsed from the beginning of the stirring process. It is then loaded into the 16 mm receptacle described above in the Hardness Method using the spatula end of a Standard Ayre Crevi-Scraper, and the Hardness is performed (starting at t=3 min. from the beginning of the stirring process, as described above).

Acceptance Under Pressure

Figure 9:
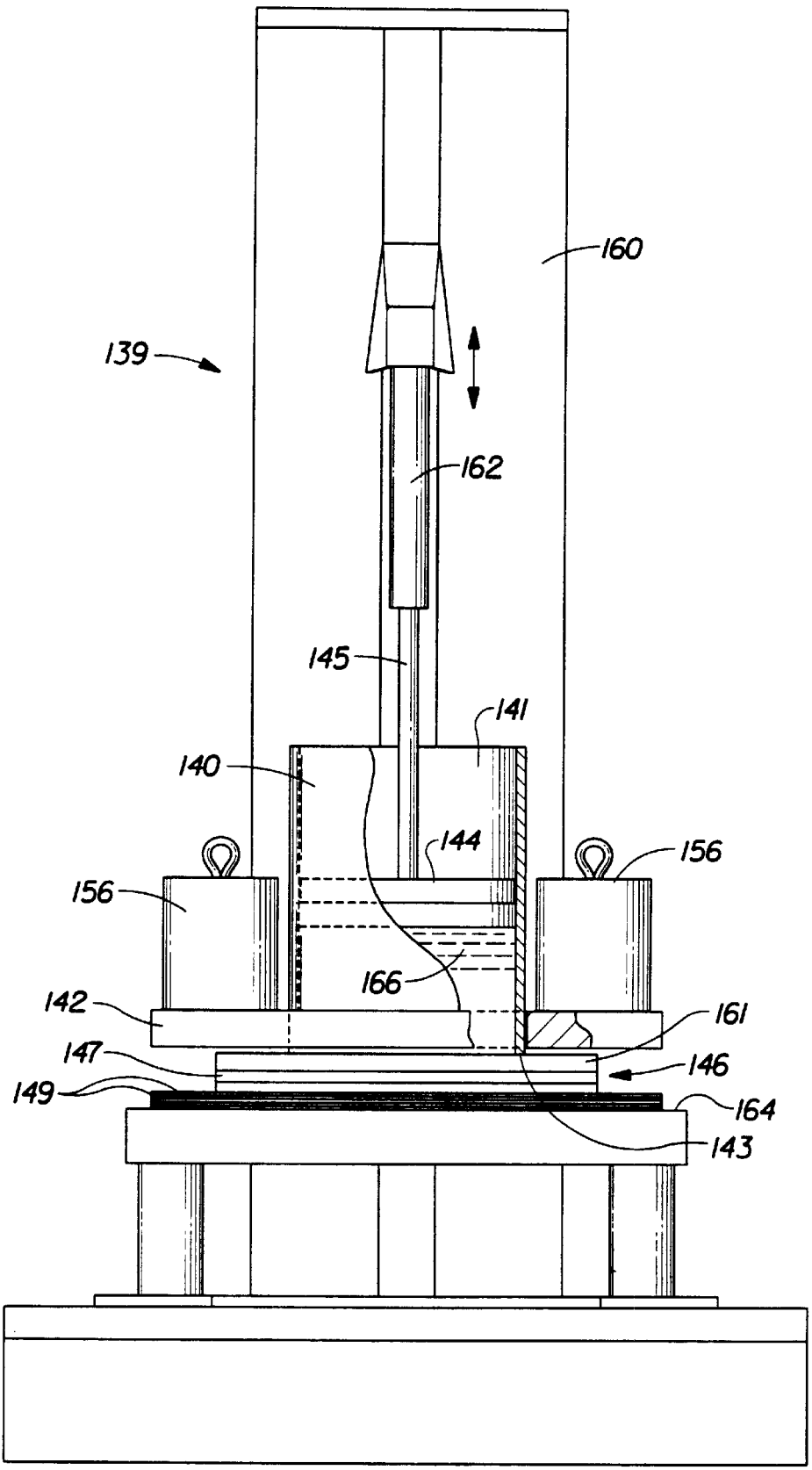
FIG. 9 is a schematic front view of an apparatus which may be used to measure Acceptance Under Pressure characteristics of certain structures.

Acceptance Under Pressure is measured by the following test which uses the apparatus 139 illustrated in FIG. 9. A hollow plexiglas cylinder 140 is provided attached to a stainless steel plate 142 about 9.5 mm thick. The plate 142 is a square, about 10.16 cm×10.16 cm (about 4 in.×4 in.). The cylinder 140 and plate combination has a height of 7.6 centimeters (about 3.0 inches), an inside diameter of 5.08 centimeters (about 2.00 inches) and an outside diameter of 6.3 centimeters (about 2.48 inches). The bottom of the cylinder 140 extends below the plate 142 a distance of about 3.5 millimeters. The lip 143 prevents the test fluid 166 from leaking outside the designated test area. Two 625 gram weights 156 are also provided, each having a diameter of 5.08 cm (about 2.0 inches).

A cylindrically shaped 24.6 gram plexiglas weight 144 is provided. The weight 144 has a diameter of 5.08 centimeters (about 2.0 inches), so that the weight 144 fits with close tolerance within the cylinder 140 but can freely slide throughout the hole 141 in the cylinder 140. This arrangement provides a pressure of about 119 Pascals (Pa) (about 0.017 pounds per square inch) and a test area of about 20.27 square cm (about 3.142 square inches). If desired, the weight 144 may have a handle 145 to allow it to be easily inserted into and removed from the cylinder 140. In such cases, the combined mass of the handle 145 and the cylindrical weight 144 should equal 24.6 grams.

Figure 10:
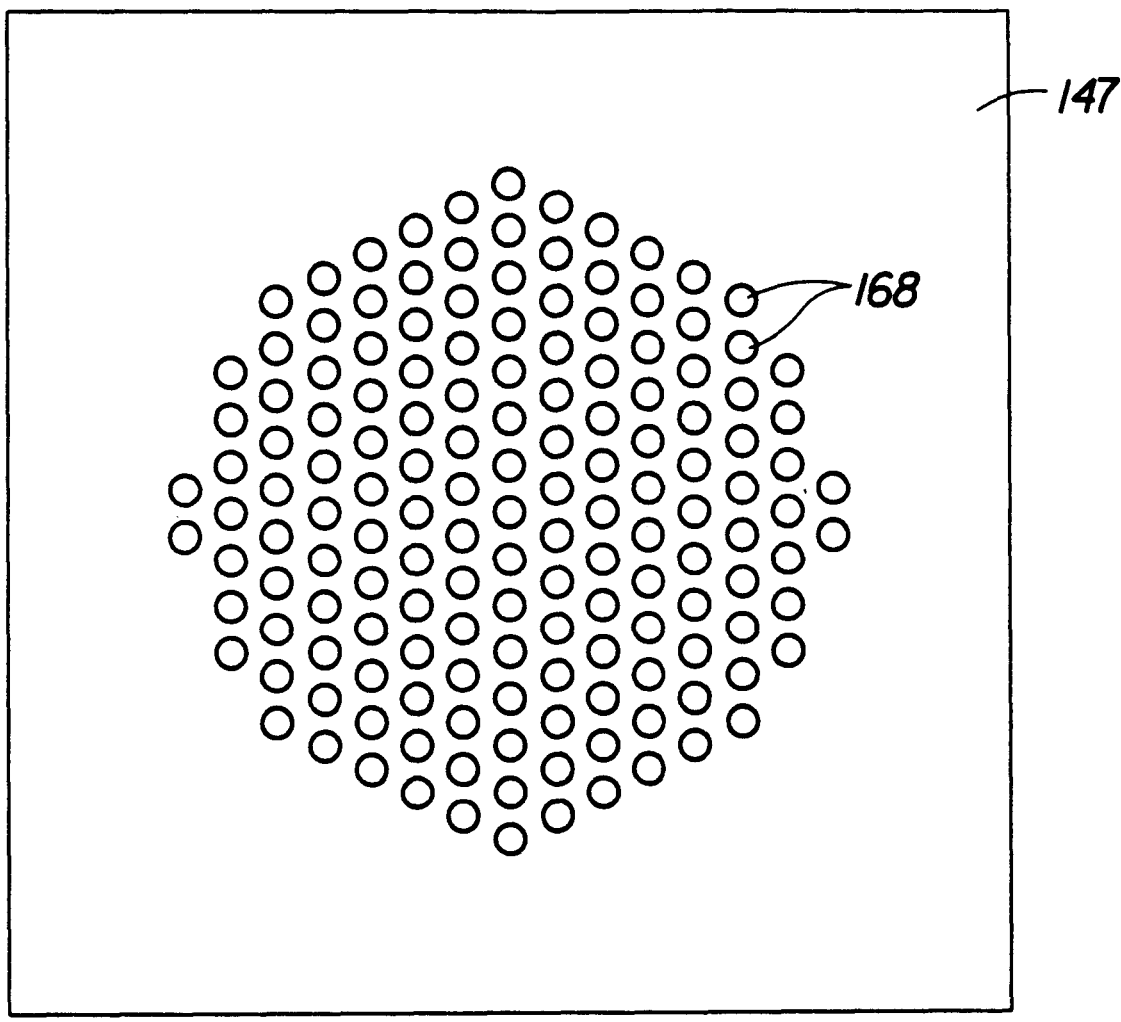
FIG. 10 is a plan view of a piece of the apparatus shown in FIG. 9.

A sample 146 of the structure to be tested for Acceptance Under Pressure properties is provided. The sample 146 may be cut from an existing diaper or may be constructed from material which has not been formed into a diaper. The sample 146 includes the entire structure intended for use in an article or the entire structure of the article to be evaluated, including the top layer 161. (In order to measure the Acceptance Under Pressure performance of discrete acceptance elements, as described in the Acceptance Element section above, the Acceptance Under Pressure test is performed using a standard storage element 147 in place of any underlying structure or layers. The standard storage element 147 used herein includes a 4 inch square 1.6 mm thick aluminum plate having a pattern of 153 regularly spaced 4.3 mm diameter holes 168, as shown in FIG. 10. The holes are arranged such that there are about 26 holes per square inch.) The sample 146 should be cut into a square measuring 10.16 centimeters by 10.16 centimeters (about 4 inches by 4 inches).

Five layers of a high basis weight blotter 149 measuring 4 inches×4 inches are provided. The top layer 161 of the sample 146 is removed and the remaining components, or layers, of the sample 146 (if there are multiple components or layers) and the five sheets of blotter material 149 are weighed to the nearest 0.01 grams. Thus, if the sample 146 is being taken from a diaper, the layers of the diaper such as topsheets, secondary topsheets, acquisition layers, absorbent cores etc., should be separated prior to weighing. (In some cases, a single layer may comprise two or more permanently bonded components.) In so doing, care must be taken not to destroy the sample 146 or cause unintended gross deformation of any parts of the sample 146. The layers of the sample 146 may be frozen to aid their separation from adjacent layers of the sample 146. Freezing may be accomplished using PH100-15 circuit refrigerant made by Philips ECG, Inc. of Waltham, Mass.

The sample 146 should be reassembled as originally configured on top of 5 stacked layers of blotter material 149 with the side of the sample 146 intended to face the wearer oriented facing up and away from the blotter material 149. The blotter material 149 is preferably filtration grade paper, available from Ahlstrom Filtration, Inc. of Mt. Holly Springs, Pa. as #632-025, having a basis weight of about 90 grams per meter.

The combined assembly of the sample 146 and the blotter material 149 is centered on the work surface 164 of a Stevens-Farnell QTS-25 Model 7113-5 kg Texture Analyzer 160 (available from Leonard Farnell Co. of Hatfield, England), under the probe 162. A suitable probe 162 is a 100 cm flat-ended cylindrical aluminum extension rod "QTSM3100" available from the Leonard Farnell Co. of Hatfield England. The cylinder 140 is centered on the sample 146. The two 625 gram weights 156 are placed on opposite comers (diagonally) of the plate 142 to stabilize it. A syringe having an opening of about 4 to 6 millimeters is used to dispense approximately 10 cubic centimeters of viscous fluid bodily waste analog 166 (Analog C as described below) through the hole 141 in the cylinder 140 onto the top of the sample 146.

Once the proper amount of feces analog 166 (Analog C) has been measured into the cylinder 140, the 24.6 gram weight 144 is inserted slowly and gently into the hole 140 in the cylinder 140 until it rests on the surface of the analog, and subsequently gently rotated one rotation clockwise followed by one rotation counterclockwise, both rotations perfomed while carefully avoiding the application of any downward forces on the weight. The Texture Analyzer 160 is activated so the probe 162 depresses the cylindrical weight 144 at a rate of 10 millimeters per minute until a resisting force of about 144.6 grams is reached. The Texture Analyzer 160 is set to stop the downward stroke once the resistance force of 144.6 grams is reached. The recorder is set to trigger at a resistive force of 5 grams. (The maximum resisting force of 144.6 grams corresponds to an applied pressure of 700 Pascals or 0.1 pounds per square inch). Once a resistive force of 144.6 grams is reached, the probe 162 is retracted to its starting position.

The weight 144 is removed from the cylinder 140, and then the cylinder 140 is removed from the surface of the sample 146, taking care not to drip any Analog C remaining in the cylinder 140 onto the sample. The top layer 161 of the sample 146 is then removed from the underlying layer(s) of the sample 146 by dragging the top layer 161 parallel to the surface of the underlying layers, if possible taking care not to drip any Analog C onto the blotter paper. For certain structures where the top layer 161 is difficult to remove by dragging parallel to the underlying layers, the top layer 161 may be peeled or lifted away from the underlying layers of sample 146. If the sample 146 comprises only a single layer, the standard acceptance element 151, described below, is utilized as the top layer 161 of the sample 146. The underlying layers of the sample 146 and the blotter material 149 are then weighed. The amount of test Analog C accepted by the sample 146 equals the increase in combined weight of the underlying layer(s) of the sample 146 and the blotter material 149 caused by the test Analog C penetrating through the top surface layer of the sample 146 per unit work performed (in milliJoules) on a unit area basis. The area under the force vs. distance curve, used in calculating the unit work, is calculated by integrating the force resisting the probe on its downward stroke over the total distance traveled until the maximum force of 144.6 grams is registered. The unit work is calculated using the following equation:

$$\text{Unit Work (mJ)} = \text{Area under the force vs. distance curve (g/mm)} \cdot (9.81 \text{ m/s}^2)/(1000 \text{ mm/m})$$

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article adapted to receive feces having a first waist region, a second waist region opposed to the first waist region, a crotch region disposed between the first waist region and the second waist region, the absorbent article comprising:

a liquid pervious topsheet;

a liquid impervious backsheet joined to at least a portion of the topsheet;

an absorbent core disposed between at least a portion of the topsheet and the backsheet;

a waste management element having an Acceptance Under Pressure value of greater than 0.50 grams of a viscous fluid bodily waste per square inch of the waste management element per millijoule of energy input; and an effective concentration of a feces modifying agent disposed in the article such that the feces modifying agent is available to contact at least a portion of the feces deposited in the article and to physically or chemically modify at least a portion of the feces deposited in the article wherein said feces modifying agent is selected from the group consisting of: sulfites, thiols, alcohols, mercaptoacetic acid, sodium thioglycolate, thiolactic acid, thioglycoamide, glycerol monothioglycolate, borohydrides, tertiary amines, thiocyanates, thiosulfates, cyanides, thiophosphates, arsenites, phosphines, betaines, hydroxylamine, and LiHB $(C_2H_5)_3$.

2. The absorbent article of claim 1 wherein the waste management element having an Acceptance Under Pressure value of greater than about 1.0 grams of a viscous fluid bodily waste per square inch of the waste management element per milliJoule of energy input.

3. The absorbent article of claim 1 wherein the waste management member includes a macro-particulate structure including a multiplicity of discrete particles having a nominal size of between about 1 mm and about 25.4 mm.

4. The absorbent article of claim 1 wherein the feces modifying agent is disposed on at least some of the discrete particles.

5. The absorbent article of claim 1 wherein the feces modifying agent is disposed in at least a portion of the waste management member.

6. The absorbent article of claim 1 wherein the feces modifying agent decreases the Hardness of at least a portion of the feces by greater than about 100% at a concentration of no more than about 0.5 weight percent.

7. The absorbent article of claim 6 wherein the decrease in Hardness takes place in no more than about 5 minutes.

8. The absorbent article of claim 1 wherein the feces modifying agent is disposed on a carrier structure.

9. The absorbent article of claim 8 wherein the carrier structure includes a web.

10. The absorbent article of claim 1 wherein the carrier structure includes a brush stricture.

11. The absorbent article of claim 1 wherein the feces modifying agent is releasably attached to at least a portion of the article.

12. The absorbent article of claim 11 wherein the feces modifying agent is releasably attached to at least a portion of the article by attachment means selected from the following group: water soluble adhesive or hydrogen bonding.

13. The absorbent article of claim 1 further including at least one three-dimensional structure joined to or extending from an element of the absorbent article, the three-dimensional structure comprising the feces modifying agent, wherein the three-dimensional structure promotes contact between the feces modifying agent and the feces.

14. The absorbent article of claim 13 wherein at least some of the three-dimensional structures comprise printed hairs.

* * * * *